US008064663B2

(12) United States Patent
Van Hoe et al.

(10) Patent No.: US 8,064,663 B2
(45) Date of Patent: Nov. 22, 2011

(54) IMAGE EVALUATION SYSTEM, METHODS AND DATABASE

(75) Inventors: Lieven Van Hoe, Aalst (BE); Bart Verweire, Evergem (BE)

(73) Assignee: Lieven Van Hoe, Aalst (BE)

( * ) Notice: Subject to any disclaimer, the term of this patent is extended or adjusted under 35 U.S.C. 154(b) by 1024 days.

(21) Appl. No.: 11/791,405

(22) PCT Filed: Dec. 1, 2005

(86) PCT No.: PCT/EP2005/012816
§ 371 (c)(1),
(2), (4) Date: Sep. 17, 2007

(87) PCT Pub. No.: WO2006/058738
PCT Pub. Date: Jun. 8, 2006

(65) Prior Publication Data
US 2008/0104116 A1    May 1, 2008

Related U.S. Application Data

(60) Provisional application No. 60/677,671, filed on May 4, 2005.

(30) Foreign Application Priority Data

Dec. 2, 2004   (WO) ................. PCT/EP2004/013684

(51) Int. Cl.
*G06K 9/00*   (2006.01)
*G06K 9/46*   (2006.01)
*G06K 9/62*   (2006.01)
*G06K 9/74*   (2006.01)
*G06F 17/00*   (2006.01)
*G06N 5/02*   (2006.01)
*G06N 7/00*   (2006.01)
*G06N 7/08*   (2006.01)

(52) U.S. Cl. ........ 382/128; 382/100; 382/203; 382/209; 382/228; 128/920; 128/922; 128/923; 706/46; 706/48; 706/50; 706/53

(58) Field of Classification Search ................... None
See application file for complete search history.

(56) References Cited

U.S. PATENT DOCUMENTS 5,852,819 A  *  12/1998  Beller .................................. 1/1
(Continued)

FOREIGN PATENT DOCUMENTS

| EP | 1 103 900 A2 | 5/2001 |
| EP | 1 315 125 A2 | 5/2003 |
| WO | WO 01/57777 A2 | 8/2001 |

*Primary Examiner* — Tom Y Lu
*Assistant Examiner* — Thomas Conway
(74) *Attorney, Agent, or Firm* — Amster, Rothstein & Ebenstein LLP

(57) ABSTRACT

The present invention relates to a method and system for evaluating at least one abnormality in one or more medical images of a subject comprising: (a) determining the location of each abnormality from pre-defined selection, (b) determining the pattern of each abnormality from pre-defined selection, (c) accessing a multidimensional database comprising data of patterns, locations, and conditions associated therewith, in which the database comprises data of each of patterns, locations, and conditions is comprised in separate dimension(s), and characteristic information for patterns, locations, and conditions is organized in the database into discrete categories, (d) extracting from the multidimensional database a list of conditions corresponding to the imaging data determined in steps (a) and (b), (e) providing an evaluation of abnormality using list obtained in step (d). The invention also relates to a database, computer program, system for navigating the database, a method for entering data into a database.

30 Claims, 28 Drawing Sheets

U.S. PATENT DOCUMENTS

| | | | |
|---|---|---|---|
| 6,032,678 A * | 3/2000 | Rottem | 600/437 |
| 6,480,842 B1 * | 11/2002 | Agassi et al. | 1/1 |
| 7,447,635 B1 * | 11/2008 | Konopka et al. | 704/275 |
| 2004/0101177 A1 * | 5/2004 | Zahlmann et al. | 382/128 |

* cited by examiner

A methodology to automatically interpret visual information using state-of-the art knowledge

Description of the abnormality:  T2

*This type of abnormality belongs to the following category (please indicate by arrow):*

A. MORPHOLOGY
  ☐ focal abnormality (single or multiple)
  ☐ diffuse disease
  ☐ abnormal size & anatomy  ⟵ 262

261 ⟶ B. UPTAKE OF CONTRAST MEDIA
  ☐ focal abnormality (single or multiple)
  ☐ diffuse disease C. FUNCTION
  ☐ flow pattern
  ☐ contraction
  ☐ other

FIGURE 26

Morphologic pattern: ⟵ 271
Specific Sublocation (optional): ⟵ 272
Specific patient subgroup (optional): ⟵ 273

Prototype example: T3

Diagnostic value of this pattern in this context: low / high ⟵ 274
Comment: ⟵ 275                                          276
            277          278          279          2710

| N° | Disease name | When you see this pattern, this disease is... | For this disease, this pattern is | Key discriminative findings + N° |
|---|---|---|---|---|
| 1 | | the first | typical / atypical | |
| 2 | | common / uncommon | typical / atypical | |
| 3 | | common / uncommon | typical / atypical | |
| 4 | | common / uncommon | typical / atypical | |
| 5 | | common / uncommon | typical / atypical | |
| Other possible diseases: ⟵ 2711 | | | | |

FIGURE 27

Morphologic pattern: focal lesion, hypervascular, homogenous

Prototype example T1

Diagnostic value of this pattern in this context: high
Comment:

| N° | Disease name | When you see this pattern, this disease is... | For this disease, this pattern is | Key discriminative findings • N° |
|----|--------------|-----------------------------------------------|-----------------------------------|-----------------------------------|
| 1 | FNH | the first | typical | - central scar (not obligate) (1)<br>- strong uptake of iron oxide particles<br>- the larger the lesion, the more likely FNH<br>- sometimes central feeding artery (2)<br>- usually iso- or hyperdense in PVP (3) |
| 2 | Adenoma | common | atypical | - if homogenous, DD with FNH difficult |
| 3 | Hypervascular metastasis | uncommon | atypical | - usually central necrosis |
| 4 | Hemangioma | uncommon | atypical | - seen only in small hemangiomas<br>- follows density / SI of blood (4) |
| 5 | HCC | uncommon | atypical | - only homogenous if small<br>- rapid washout of contrast (5) |

Other possible diseases: intrahepatic splenosis, AVM, pseudoaneurysm; aneurysm

FIGURE 32

Addendum to previous slide  T2

Images illustrating key discriminative findings
(numbers should correspond to description on previous page)

(2)   (3)

FNH: Isodense to parenchyma but hypodense to vessels
In PVP
- follows density / SI of blood (4)
- rapid washout of contrast (5)

Optional: variants of this pattern and their significance:
• focal lesion <2cm, hypervascular, homogenous: hemangioma, HCC, metastasis more likely
•

Optional: key reference:

FIGURE 33

| | Morphologic pattern: focal lesion, ring enhancement | | | Prototype example T1  |
|---|---|---|---|---|
| | Diagnostic value of this pattern in this context: low / high  Comment: | | | |
| N° | Disease name | When you see this pattern, this disease is... | For this disease, this pattern is. | Key discriminative findings + N° |
| 1 | Metastasis | the first | typical | - multiplicity<br>- sometimes primary tumor can be detected (1) |
| 2 | HCC | common | atypical | - cirrhosis<br>- alfa-feto protein |
| 3 | Cholangiocarcinoma | common | typical | - biliary dilatation (sometimes)<br>- delayed central enhancement |
| 4 | Abscess | common | typical | - double target sign in 40% (2) |
| 5 | Hemangioma | uncommon | atypical | - multiphase imaging shows progression from globular to thick rim to complete enhancement (3) |
| Other possible diseases: | | | | |

FIGURE 34

Addendum to previous slide                                             T2

Images illustrating key discriminative findings
(numbers should correspond to description on previous page)

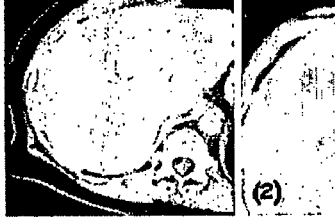

Optional: key reference: Gabata AJR 2001; 176: 675-679

FIGURE 35

Addendum to previous slide    T2

Images illustrating key discriminative findings
(numbers should correspond to description on previous page)

(3)

Optional: variants of this pattern and their significance: focal lesion with slight signal loss on T2 weighted images after administration iron oxide particles (<30% SI drop). Additional diagnostic possibilities: adenoma, hepatocellular carcinoma Optional: key reference:

Prototype example T1

Morphologic pattern:
focal lesion with fluid-fluid level

Diagnostic value of this pattern in this context: high
Comment:

| N° | Disease name | When you see this pattern, this disease is... | For this disease, this pattern is | Key discriminative findings + N° |
|---|---|---|---|---|
| 1 | Abscess | the first | typical | - thick wall, double target sign (best seen in arterial phase) (1)<br>- clinical context |
| 2 | Hematoma | uncommon | atypical | - clinical context |
| 3 | Cystic metastases | Uncommon (very rare) | atypical | - multiplicity (2) |
| 4 | | common<br>uncommon | typical<br>atypical | |
| 5 | | common<br>uncommon | typical<br>atypical | |
| Other possible diseases: | | | | |

FIGURE 41

Addendum to previous slide — T2

Images illustrating key discriminative findings
(numbers should correspond to description on previous page)

(1)   

Double target sign
in MRI
AP versus PVP II

Optional: key reference:

FIGURE 42

Addendum to previous slide — T2

Images illustrating key discriminative findings
(numbers should correspond to description on previous page)

Metastases of amelanotic malignant melanoma (2) 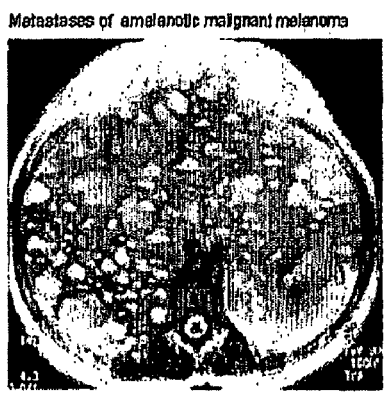 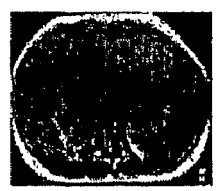 

Optional: key reference:

FIGURE 43

IMAGE EVALUATION SYSTEM, METHODS AND DATABASE

This is a U.S. national phase of PCT Application No. PCT/EP2005/012816, filed Dec. 1, 2005 and claims priority to PCT Application No. PCT/EP2004/013684, filed Dec. 2, 2004 and U.S. Provisional Application No. 60/677,671, filed May 4, 2005.

FIELD OF THE INVENTION

The present invention is in the field of evaluation of abnormalities in images, image databases and method of data entry.

BACKGROUND TO THE INVENTION

Radiologists are medical doctors who are capable of interpreting images such as those obtained by conventional radiology, ultra-sonography (US), computed tomography (CT), and magnetic resonance imaging (MRI). As these imaging techniques have rapidly evolved technically, more and more anatomical details are available to be assessed non-invasively. For practicing radiologists, it can be difficult to be aware of all possible imaging presentations of all possible diseases. It is estimated that typically a clinical radiologist seeks diagnosis or anatomy assistance on 5-10% of cases daily. The problem is that referring to reference books, web searches, or colleagues interrupts work flow and reduces productivity. Although all information needed by the radiologist to make the correct diagnosis is usually available "somewhere", the radiologist faces three problems with regard to obtaining this information as follows.

First, it may be difficult and/or time consuming to find the information required. Typically, a relevant imaging library contains hundreds of books and journals. It is not possible for an individual to catalogue or remember the precise content of all these books and journals. Internet searches are not necessarily more efficient: usually a query generates a large number of matches; finding the best match necessarily takes time and effort.

Secondly, the information may be fragmented, e.g. there may be basic information about a specific disease in a textbook, while for more detailed information dedicated Internet searches or other books may be required. Thus, even if the user knows where to find the information, finding the complete information he needs may not be straightforward.

Finally, most information is not presented in an optimal way. In clinical practice, the radiologist is confronted with specific morphologic patterns of disease at specific locations. As an example, he may see a "ring-enhancing focal lesion" (pattern) in the "brain" (location). In our hypothetical example, the radiologist would be interested to find information about brain and "ring-enhancing focal lesion", with a description of different (common and uncommon) diseases that can cause this structural abnormality. He would further like to read a discussion of the relative likelihood of these diseases, means to differentiate between these diseases, and further information about each disease. Unfortunately, most radiology textbooks and other sources only provide a systematic overview of diseases according to location. For example, a radiological textbook focusing on liver diseases will describe the most important diseases one by one. In order to find out to what disease best matches a certain morphologic pattern, the radiologist first needs to have an a priori knowledge about which diseases could cause that pattern, and, secondly, has to find where exactly these diseases are discussed in the book (or other medium), and whether or not the description of imaging findings in this reference text indeed corresponds to his "case". Such a search may be quite straightforward in some cases while it may be quite time-consuming and frustrating in others. Also, even the most recently developed databases on the Internet are organized by location, not by location and pattern.

Furthermore, information in most radiology textbooks and other references is not structured according to the work flow of the radiologist and finding practical information is difficult. FIG. 4 illustrates the steps presently required when a radiologist confronted with an abnormality at a certain location/sublocation and with a particular morphologic pattern wants to identify the corresponding disease(s). For difficult cases, he has to find an appropriate textbook to identify the diseases that may be present with a pattern similar to the one he has identified. During this process, the radiologist creates a list of possible diagnoses (Diagnosis 1 to n), from which the diseases that do not result in the appropriate pattern are eliminated. This list can further be refined by matching the clinical status of his particular patient (e.g., male or female) with the patient-related information provided for the different diseases (e.g. Disease No 1 tends to occur in women). It is clear that this is a quite inefficient process.

CASE EXAMPLE

In order to illustrate the problems mentioned above, we provide an example in which a radiologist is confronted with a ring-enhancing lesion in the brain in a 27-year-old man complaining of headaches (FIG. 1). Previous history reveals no specific health problems. Our radiologist is not an expert neuroradiologist and does not exactly know what diagnosis to suggest. The referring physician is anxious to get the result of the imaging study. The colleague neuroradiologist is on holiday. The radiologist may first consult a textbook on neuroradiology. After a relatively short but intensive search, he finds the department's neuroradiology reference manual. The index is first searched for "ring-enhancing lesion". Unfortunately, no such term is indexed. Because he needs an answer, there is no way other than to proceed page by page through the book and look for similar examples (images). After several minutes of searching, he may find a number of possible diagnoses: high-grade glioma (discussed in chapter 13), atypical meningioma (chapter 14), lymphoma (chapter 14), leukaemia (chapter 14), metastasis (chapter 14), abscess (chapter 7), radiation necrosis (chapter 16), multiple sclerosis (chapter 5), ADEM (chapter 5), and glioblastoma multiforme (chapter 13).

Not completely satisfied with the result and still lacking a "primary diagnosis", he may need to make use of the Internet. Entering "ring-enhancing lesion" and "brain" in a search engine results in 533 hits. The results mentioned as closest hits are available as an abstract only, and the full text is not available. Moreover, most of them are case studies and irrelevant for the question. So, this does not really help either.

To answer the question, he may use a proprietary online database containing papers published in a major radiology journal. In the present example, the same search results in 4 hits. None of the papers really provides a focused answer. Currently available online databases provide cases and diagnoses organized by location of abnormality. The radiologist using such a database has to choose the appropriate location and obtains a (usually large) large list of possible diagnoses (FIG. 5). In the best of available systems, the user can then further refine this list by entering specific information relating to the patient or the imaging findings, however, such diagnoses are inefficient and inaccurate.

Thus, although the radiologist knows that the information he needs is available, he is not able to locate it. When the referring physician phones back, the radiologist states that, in such a case, one cannot differentiate between tumor and inflammation. In order to illustrate his knowledge, he mentions the possibility of glioblastoma multiforme, high-grade glioma, ADEM, multiple sclerosis, abscess, and other entities. The radiologist cannot make a clear diagnosis and is forced to defer making his report until the following morning. His neuroradiology colleague will likely be able to tell him whether his preliminary report was somewhat accurate, or not accurate at all.

Concluding our discussion of the prior art, the present workflow of the radiologist is schematically represented in FIG. 2. As can be seen, there are several factors that an operator would need consider such as the image for the current case and reference material. The quality of the final diagnosis largely depends on all of these factors, with the experience of the operator being a major factor. Only very experienced operators could be expected to have a wide knowledge of medical images and the disorders related thereto, so making an effective diagnosis.

The present invention aims to overcome the disadvantages of the prior art, by providing a system and method for evaluating medical imaging data (and non-imaging data), which follows the natural work flow of the operator, and provides fast, accurate and informative diagnoses.

BRIEF DESCRIPTION OF THE FIGURES

FIGS. 24 to 28: Example of a blank template suitable for data entry by an expert.

FIGS. 29-43: Examples of partially or fully completed data-entry templates, relevant to patterns located in the liver.

DETAILED DESCRIPTION OF THE INVENTION

The present invention relates to a method and system for evaluating medical imaging and optionally non-medical imaging data of a subject. Such evaluation assists in the diagnosis of conditions or diseases of the subject. The invention also relates to a computer program implementing the method, a database, and a navigation system for extracting or visualising information from the database.

Figure 8:
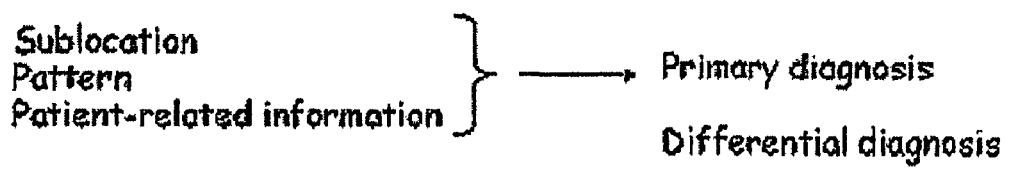
FIG. 8: Use of the present invention

The imaging data relates to at least one abnormality present in one or more medical images of the subject being diagnosed. The abnormality may be characterised by the operator of the invention, for example, in terms of the type of abnormality (the pattern) and/or the location of the abnormality (e.g. the organ, tissue or other location information). The pattern may be, for example, a morphological pattern of the abnormality (e.g. T2 hyperintense, T1 hypointense, peripherally calcified, irregular etc. derivable from one or more medical images of a subject). Alternatively, the pattern may be a non-morphological pattern of the abnormality (e.g. time-intensity curve of contrast uptake, flow curve, muscular contraction pattern etc. also derivable from one or more medical images of a subject). Such data is used as input in a database search to provide a primary diagnosis or list of diagnoses (FIG. 8).

One embodiment of the invention is a method and system for assisting with the diagnosis of a patient wherein the location of the abnormality is chosen from a pre-defined selection (e.g. a body location template). For example, locations may include but are not limited to any of liver, lung, bladder, kidney, brain, spleen, breast, testes, prostrate, colon, stomach, throat, intestine, skin, ovary. Locations may be further restricted by sub-location which refers a position within the location e.g. a part of the brain. The predefined selection may be organised alphabetically, according to location, or organ system etc. A hierarchical selection of locations starting with broad grouping is within the scope of the invention. For example the operator may be presented with a broad group of location categories (e.g. central nervous system, musculoskeletal system, circulatory, digestive, respiratory, reproductive, endocrine, urinary) from which subgroups may be selected (e.g. knee, fibula, tibia for the category of musculoskeletal system). At the lowest hierarchical level, the precise location may be selected (e.g. meniscus for the knee). Table 1 shows examples of possible organ systems, locations and sublocations according to a method and system of the present invention. An example of a hierarchical organisation is also depicted.

TABLE 1

Possible organ systems, locations, sublocations and hierarchical organisation of data entry choices according to a method and system of the present invention.

| ORGAN SYSTEM | BODY LOCATION | EXAMPLES OF SUBLOCATIONS |
|---|---|---|
| Brain & skull | Skull (not base) | bone ans soft tissue |
| Brain & skull | Skull base | incl anterior skull base, sphenoid, clivus, jugular foramen, other foramina |
| Brain & skull | Spaces | extradural space, subdural space, subarachnoidal space, basal cisterns |
| Brain & skull | Meninges | meninges |
| Brain & skull | Veins | veins, sinuses |
| Brain & skull | Cerebral hemispheres: parenchyma | cortex, white matter, temporal, parietooccipital, frontal |
| Brain & skull | Midline supratentorial parenchyma | corpus callosum |
| Brain & skull | Basal ganglia | basal ganglia |
| Brain & skull | Ventricles | lateral ventricles, third, fourth |
| Brain & skull | Sella | pituitary |
| Brain & skull | Suprasellar region | pituitary stalk, hypothalamus |
| Brain & skull | Parasellar region incl. cavernous sinus | |
| Brain & skull | Meckel's cave | meckel's cave |
| Brain & skull | Pineal gland | pineal gland |
| Brain & skull | Cerebellum & infratentorial space | cerebellum |
| Brain & skull | Brain stem | mesencephalon, pons, medulla oblongata |
| Brain & skull | Arteries | |
| Brain & skull | Nerves | |
| Brain & skull | Orbit | globe, extraocular intraconal space, extraocular extraconal space |
| spine | Medulla | medulla |
| spine | Intradural extramedullary space | intradural extramedullary space |
| spine | Extradural space other than vertebrae and disks | Extradural space other than vertebrae and disks |
| spine | Vertebrae and disks | Vertebrae, disks, facet joints |
| Head & Neck | EAC | EAC |
| Head & Neck | Temporal bone | Middle ear incl oval window, mastoid, Inner ear, Petrous apex, facial nerve |
| Head & Neck | CPA and IAC | CPA, IAC |
| Head & Neck | Paranasal sinuses & nasal cavity | Paranasal sinuses, nasal cavity |
| Head & Neck | Nasopharynx | nasopharynx |
| Head & Neck | Oropharynx | oropharynx |
| Head & Neck | Hypopharynx | oropharynx |
| Head & Neck | Oral mucosal space | |
| Head & Neck | Sublingual space | |
| Head & Neck | Submandibular space | |
| Head & Neck | Mandible & maxilla | |
| Head & Neck | PPS | |
| Head & Neck | Masticator space | |
| Head & Neck | TMJ | |
| Head & Neck | Parotid space | |
| Head & Neck | Carotid space | |
| Head & Neck | Retropharyngeal space | |
| Head & Neck | Perivertebral space | |
| Head & Neck | Infrahyoid cervical spaces | anterior, posterior |
| Head & Neck | Larynx | vocal cords, epiglottis and AEF, sm space & cartilage, paraglottic |
| Head & Neck | Thyroid & parathyroid | thyroid, parathyroid |
| Head & Neck | Airways, esophagus | cervical trachea, esophagus |
| Chest | Thoracic wall | |
| Chest | Pleura | |
| Chest | Breast | |
| Chest | Mediastinum | Anterior, middle, and posterior mediastinum, trachea, vessels |

TABLE 1-continued

Possible organ systems, locations, sublocations and hierarchical organisation of
data entry choices according to a method and system of the present invention.

| ORGAN SYSTEM | BODY LOCATION | EXAMPLES OF SUBLOCATIONS |
|---|---|---|
| Chest | Lung | |
| Chest | Heart, muscles and cavities | |
| Chest | Heart, valves | |
| Chest | Heart, pericardium | |
| Chest | Heart, coronary vessels | |
| Abdomen & pelvis | Liver | |
| Abdomen & pelvis | Bile ducts | |
| Abdomen & pelvis | Gallbladder | |
| Abdomen & pelvis | Pancreas | |
| Abdomen & pelvis | Kidney | |
| Abdomen & pelvis | Adrenal gland | |
| Abdomen & pelvis | Spleen | |
| Abdomen & pelvis | Stomach | |
| Abdomen & pelvis | Duodenum | |
| Abdomen & pelvis | Small bowel | |
| Abdomen & pelvis | Upper abdominal fat | omentum, ligaments, mesentery |
| Abdomen & pelvis | Appendix | |
| Abdomen & pelvis | Colon | |
| Abdomen & pelvis | Peritoneal space | |
| Abdomen & pelvis | Retroperitoneum | arteries, veins, ureters, lliopsoas space |
| Abdomen & pelvis | Adnexa | |
| Abdomen & pelvis | Uterus | corpus uteri, cervix |
| Abdomen & pelvis | Bladder and urethra | |
| Abdomen & pelvis | Prostate and Seminal vesicles | |
| Abdomen & pelvis | Testis | |
| Abdomen & pelvis | Pelvic floor | |
| Abdomen & pelvis | Intrapelvic fat | mesocolon |
| Abdomen & pelvis | Abdominal wall | |
| Abdomen & pelvis | Inguinal area | |
| Musculoskeletal | Bone & marrow (general) | |
| Musculoskeletal | Soft tissue (general) | |
| Musculoskeletal | Shoulder, periarticular bone | |
| Musculoskeletal | Shoulder, rotator cuff | |
| Musculoskeletal | Shoulder, glenohumeral joint | |
| Musculoskeletal | Shoulder, acromioclavicular joint | |
| Musculoskeletal | Shoulder, labrum & glenohumeral ligaments | |
| Musculoskeletal | Sternoclavicular joint | |
| Musculoskeletal | Elbow, periarticular bone | |
| Musculoskeletal | Elbow, joint space | |
| Musculoskeletal | Elbow, ligaments, bursae, nerves | |
| Musculoskeletal | Elbow, tendons | |
| Musculoskeletal | Wrist, periarticular bone | |
| Musculoskeletal | Wrist, joint spaces & cartilage | |
| Musculoskeletal | Wrist, ligaments | |
| Musculoskeletal | Wrist, tendons | |
| Musculoskeletal | Wrist, carpal tunnel & Guyon's canal | |
| Musculoskeletal | Hand, periarticular bone | |
| Musculoskeletal | Hand, joint spaces | |
| Musculoskeletal | Hand, tendons | |
| Musculoskeletal | Hand, ligaments | |
| Musculoskeletal | Pelvic girdle, bones | |
| Musculoskeletal | Pelvic girdle, sacroiliac joint | |
| Musculoskeletal | Pelvic girdle, symphysis pubis | |
| Musculoskeletal | Pelvic girdle, muscles & tendons | |
| Musculoskeletal | Hip, periarticular bone | |
| Musculoskeletal | Hip, joint space & labrum | |
| Musculoskeletal | Hip, muscles, tendons, bursae | |
| Musculoskeletal | Knee, periarticular bone | |
| Musculoskeletal | Knee, menisci | |
| Musculoskeletal | Knee, cruciate ligaments | |
| Musculoskeletal | Knee, collateral and other ligaments, capsule | |
| Musculoskeletal | Knee, joint spaces | |
| Musculoskeletal | Knee, cartilage | |
| Musculoskeletal | Knee, tendons & bursae | |
| Musculoskeletal | Knee, popliteal fossa | |
| Musculoskeletal | Ankle & foot, periarticular bone | |
| Musculoskeletal | Ankle & foot, joint spaces | |
| Musculoskeletal | Ankle & foot, ligaments | |
| Musculoskeletal | Ankle & foot, tendons | |
| Musculoskeletal | Ankle & foot, joint spaces | |

One embodiment of the invention is a method and system for assisting with the diagnosis of a patient wherein imaging data is selected from a pre-defined selection (e.g. a pattern template). It is aspect of the invention that said patterns in the pre-defined selection are divided into categories according to the morphology of the abnormality, uptake of contrast media by the abnormality or function of the abnormality. Thus, the pattern may chosen from a predefined selection of morphological patterns (e.g a focal lesion, multiple focal lesions, diffuse disease, abnormal size or anatomy, etc). In addition, it may be chosen from a predefined selection of patterns of contrast uptake (e.g presence or absence, time-related intensity curve, etc). It is another aspect that the patterns in the pre-defined selection may be morphological patterns only. The predefined selection may be organised alphabetically, according to type of scan, according to the pattern group, etc. A hierarchical selection of patterns starting with broad grouping is within the scope of the invention. For example the operator may be presented with a broad group of morphological patterns (e.g. Focal and Multi-focal lesions, Regional and diffuse disease, Abnormalities in size and congenital disorders) from which subgroups may be selected. At the lowest hierarchical level, the pattern may be selected (e.g. T1 hypo intense lesion, T1 hyper intense lesion, T2 hypo intense lesion, lesions with mixed signal intensity). Examples of pattern groups and patterns defined for the liver location according to the present invention are shown in Table 2 below. An example of a hierarchical organisation of pattern groups and patterns is also indicated.

TABLE 2

Examples of pattern groups and patterns, and a hierarchical organisation of data entry choices defined for the liver location according to the present invention.

| PATTERN GROUP | PATTERN |
| --- | --- |
| Focal - patterns of enhancement | Focal lesion, hypervascular, heterogenous |
| | Focal lesion, hypervascular, homogenous |
| | Hypervascular lesion in abnormal liver |
| | Hypervascular lesion with triangular configuration adjacent to capsule |
| | Focal lesion, ring enhancement |
| | Focal lesion, atypical interrupted peripheral enhancement |
| | Focal lesion, globular enhancement |
| | Focal lesion, hypovascular (PVP) |
| | Focal lesion with delayed enhancement |
| | Focal lesion without signal loss on T2 weighted images after administration iron oxide particles |
| | Focal lesion with significant signal loss on T2 weighted images after administration iron oxide particles |
| | Focal lesion with signal increase on T1 weighted images after administration iron oxide particles |
| Focal - patterns of tissue composition | Focal lesion containing calcifications |
| | Focal lesions with pure fluid content |
| | Focal lesion containing air |
| | Focall lesion with (pseudo)capsule |
| | Focal lesion causing capsular retraction |
| | Focal lesion with fluid-fluid level |
| | Focal lesion with cystic and (enhancing) solid components |
| | Fat-containing focal lesion |
| | Focal lesion with central scar |
| | Focal lesion penetrated by vessels |
| | Focal lesion with cystic components and septa (US) |
| | Hypoechoic focal liver lesion |
| | Focal lesion, hyperechoic |
| | Focal lesion with fluid density on CT but without typical US features for cyst |
| | Focal lesion with T1 hyperintense components |
| | Focal lesion (nearly) isointense on unenhanced T1 and T2 weighted images |
| | Noncystic lesion with high signal intensity on MR image with long TE (>150 msec) |
| | Noncystic lesion with high signal intensity on MR image with short TE (<100 msec) |
| Regional/diffuse abnormalities | Subcapsular/perihepatic hemorrhage |
| | Decreased parenchymal echogenicity (US) |
| | Increased parenchymal echogenicity (US) |
| | Increased parenchymal density (CT) |
| | Periportal cuffing |
| | Irregular contours of liver |
| | Decreased parenchymal density (CT) |
| | Decreased parenchymal SI (mr) |
| Size/anatomy | Small or invisible hepatic veins |
| | Enlarged hepatic veins |

The pattern list may also be restricted, based on the input of the location. For example, if the location is the liver, the operator may be presented with a selection of patterns pertinent to the liver.

The limited choice of patterns and locations enables the operator to clearly describe the abnormality, and also provides more precisely defined terms for searching the database.

The medical images can be obtained by any means of the art. Examples of types of medical images include, but are not limited to computer tomography images (CT or CAT scan), positron emission tomography images (PET scan), magnetic resonance imaging scans (MRI), ultrasound images, X-ray images. Such images may be combined with computer enhancement methods, computer predictive methods, chemical markers, contrast agents etc., all known to the person skilled in the art. It is an aspect of the invention that the predefined selection of patterns is further defined by the modality of the medical image. A description of a pattern may thus further indicate the imaging modality e.g. ultrasound, computed tomography, X-ray, magnetic resonance, angiogram or other imaging technique.

The non-imaging data relates to other patient information such as the sex of patient, age, ethnicity, immune status and oncological antecedents. Such data may be chosen from a predefined list of choices (e.g. sex (M/F), ethnicity (English, Chinese, American, Polish, Indian, Jewish, Asian, South African, Jamaican, etc)). Such limited choice enables the operator clearly to define the other aspects of the patient. Furthermore, the categorisation of features also provides more clear terms for searching. Optionally, some non-imaging data may be provided as free text description. The non-imaging data may also used as input in a database search. Examples of types non-imaging data according to the present invention are shown in Table 3 below. An example of a hierarchical organisation of the parameters and possible choices therefrom are also indicated, as are explanatory comments which may be presented to the operator.

It is an aspect of the invention that the user of the interactive expert system will be requested to enter specific non-imaging data only for those combinations of location and pattern where the lists of corresponding diseases vary in function of these non-imaging data. As an example, for the location "adrenal gland" and pattern "solid lesion", metastatic disease will be a primary diagnostic consideration in patients with malignant antecedents (particularly lung cancer), while it will only be a secondary consideration in patients without malignant antecedents.

The creation of an interactive software tool capable of providing separate lists of possible diseases for different choices of non-imaging data by the user is made possible by the multidimensional nature of the database (one additional dimension per parameter), as is explained below.

toma, Schwannoma, Metastasis, Neurofibroma, Hemangioma, Lipoma, Glioblastoma multiforme, Ganglioglioma, Glioma, Neuroma, Osteoblastoma for the category of neoplastic). Such discrete categorisation provide the database with a robust structure, particularly suitable for rapid searching and finding associations.

By organising the imaging and non-imaging data into discrete categories, the burden of describing the abnormality and non-imaging data by the operator of the invention is alleviated. There is no need to use descriptive free text which could otherwise contain subjective terms not recognised by the database or other operators. Furthermore, categorisation allows the database to be searched quickly and accurately, since data therein is already structured into the same discrete categories.

Furthermore, the use of discrete categories permits the language or definitions of the input choices to be easily switched. The interface with the operator may be selectable to provide choices such as Latin named categories, English named categories, or a set of synonyms associated with a particular branch of medicine. It also enables the output of the categorised conditions to be provided in a different lexicon. Such flexibility permits the invention to operate at different levels of understanding, with experts having different specialisations, and in different languages.

Another embodiment of the present invention is a database, comprising data regarding conditions already diagnosed and associated with at least one abnormality present in a medical image of a subject suffering from the condition. The pattern, the location, and condition associated with the abnormality are categorised in the database according to a discrete selection of patterns, location and condition possibilities. For example, each abnormality may be categorised according to a

TABLE 3

Examples of types non-imaging data, a hierarchical organisation of data entry choices and explanatory comments according to the present invention.

| PARAMETER | POSSIBLE CHOICES | COMMENT |
| --- | --- | --- |
| Age | Neonate | from birth to 4 weeks |
|  | Infant | not able to walk and talk (baby) |
|  | Child | from birth to puberty |
|  | Adolescent | from puberty to maturity |
|  | Adult |  |
|  | Elderly | older than 65 years |
| Sex | Male |  |
|  | Female |  |
| Area (continent) | Europe |  |
|  | Africa |  |
|  | Asia |  |
|  | North-America |  |
|  | South-America |  |
|  | Oceania |  |
| Immune status | Normal | not immune-compromised |
|  | Abnormal | immune-compromised |
| Oncologic antecedents | No known malignant tumor | patient has no known malignancy |
|  | Known malignant tumor | patient has a known malignant tumor or has malignant antecedents |

It is an aspect of the invention that the condition data is also organised into discrete categories. The categories may be organised into hierarchical lists such as, for example, one or more of Neoplastic, Infectious, Inflammatory, Metabolic, Traumatic, Vascular, Ischemic, Degenerative. Each top level category may be subdivided into one or more lower level categories (e.g. one or more of Lymphoma, Oligodendroglioma, Meningioma, Astrocytoma, Ependymoma, Hemangioblastoma, Chordoma, Craniopharyngioma, Medulloblaspattern type (e.g. one of T2 hyperintense, T1 hypointense, peripherally calcified, etc.), according to location (e.g. one of liver, kidney, spleen, etc.) and condition (e.g. one of lymphoma, oligodendroglioma, meningioma, astrocytoma, ependymoma). Hierarchical structuring of the categories is within the scope of the invention, as described above. The database thus comprises a structured organisation of pre-diagnosed conditions and their associated patterns and locations.

It is an aspect of the invention that the discrete categories are expandable or contractable according to the new methods of imaging, new pattern categories, new imageable abnormalities, new conditions etc.

According to an aspect of the invention, the database further comprises non-imaging information in respect of conditions already diagnosed in a subject suffering from the condition. Such non-imaging information may be in the form of discrete categories (e.g. sex, race, age, immune status, oncological antecedents) or numerical or textual, non-categorisable information.

Multidimensional Database

Figure 1:
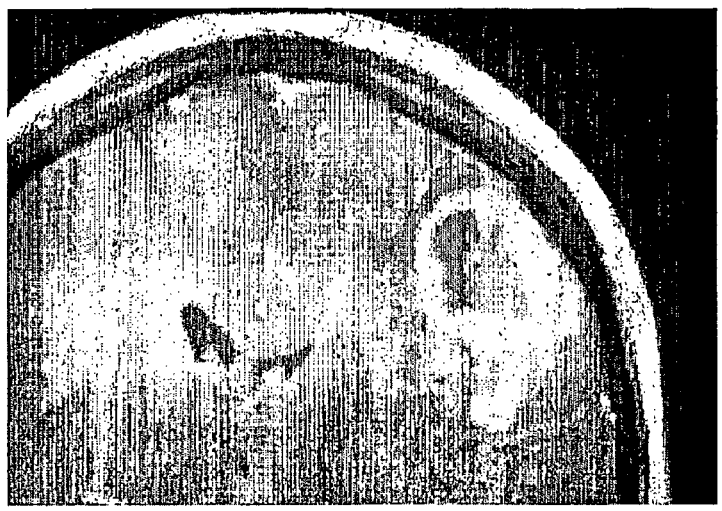
FIG. 1: Example of a ring-enhancing lesion in the brain with small satellite lesion
Figure 2:
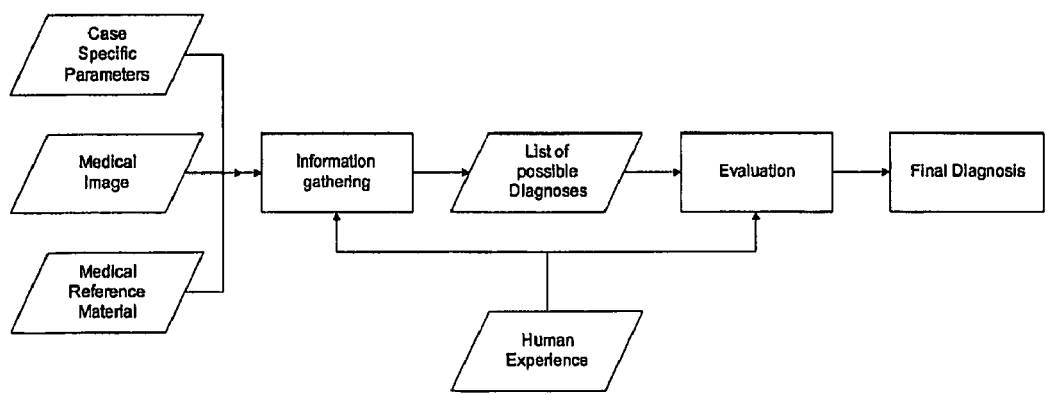
FIG. 2: Current work flow for Radiological Care
Figure 3:
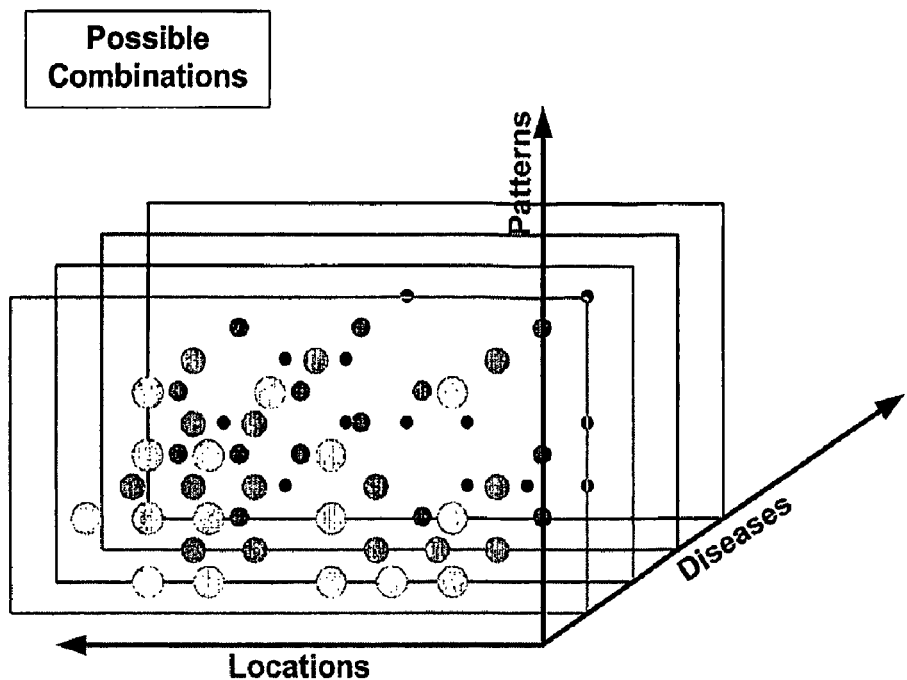
FIG. 3: Visualization of the possible combinations of Locations, Patterns and Diseases. Large circles indicate disease on the disease-axis closer to the origin, smaller circles are more distant from the disease-axis origin.
Figure 4:
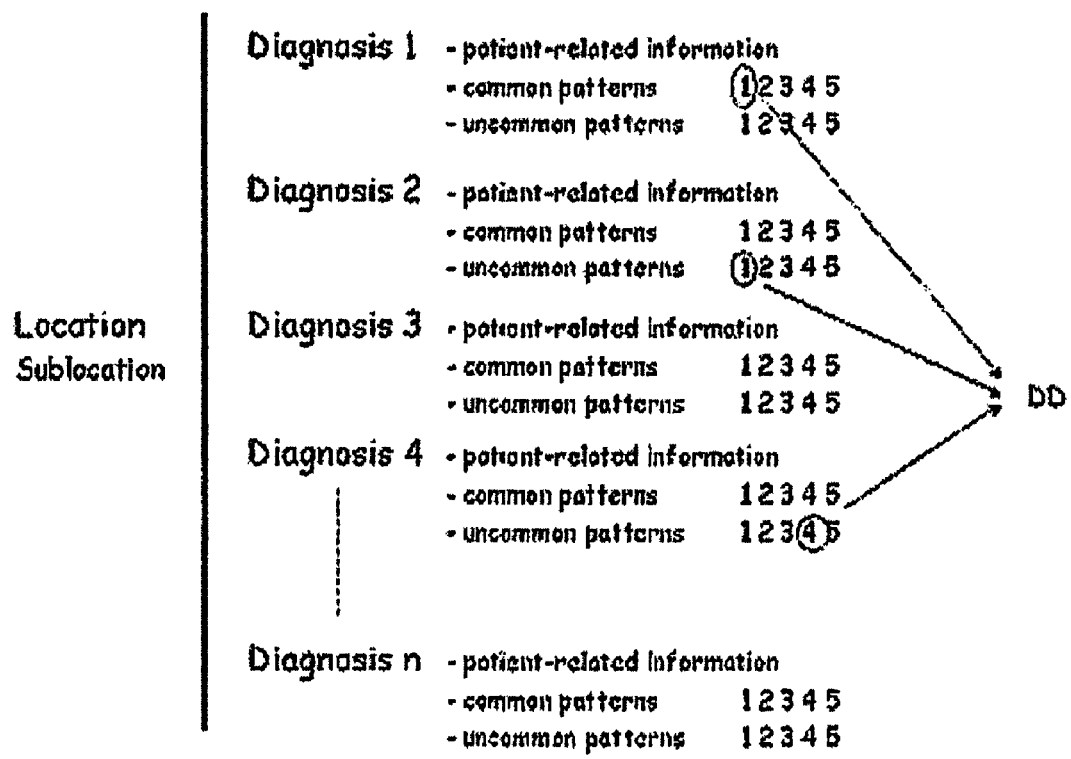
FIG. 4: Shows typical presentation of information in radiology textbooks and other reference materials. The description of morphologic presentations of different diseases (patterns) is scattered within the text. Finding relevant information (i.e. finding all diseases that may result in a certain pattern at a certain location) may be a time-consuming task.
Figure 5:
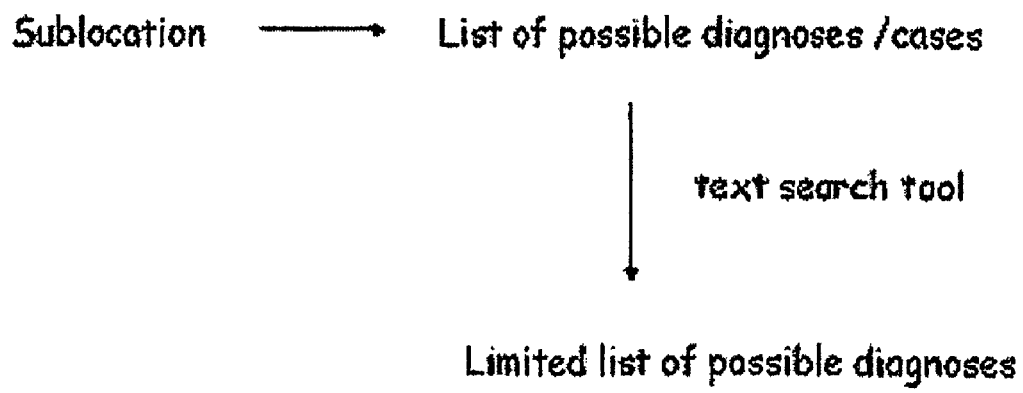
FIG. 5: Steps required when the radiologist consults an existing online database or expert system.

A database according to the invention is preferably a multidimensional database. A multidimensional database provides at least one dimension for each of condition, location and pattern. A database of the invention comprises all possible combinations of locations, patterns and conditions to which specific attributes and more detailed information are attached. Such organisation can be visualised in FIG. 3, which depicts a 3-dimensional arrangement of data with one dimension (axes) for locations, patterns and conditions. Each circle in FIG. 3 corresponds to a particular combination of a location, pattern and condition. Four diseases are shown (4 planes). Circles of the same size are part of the plane represented by rectangles in the disease-axis, and correspond to the same condition. Not all combinations of any two of these parameters result in a valid combination—an absent circle indicates no data for a particular combination. Although the database is depicted as a three dimensional array in the FIG. 3, it is purely for illustrative purpose. Means for organising multidimensional data in multidimensional databases and database management system are known in the art and any are within the scope of the invention.

The number of dimensions in a multidimensional database is at least 3, and may be 4, 5, 6, 7, 8, 9, 10 or more than 10. The number of dimensions depends on the number of patient-related parameters taken into account. The number of dimensions can be variable and optimised for all combinations Location, Pattern Condition, and other relevant parameters.

Figure 6:
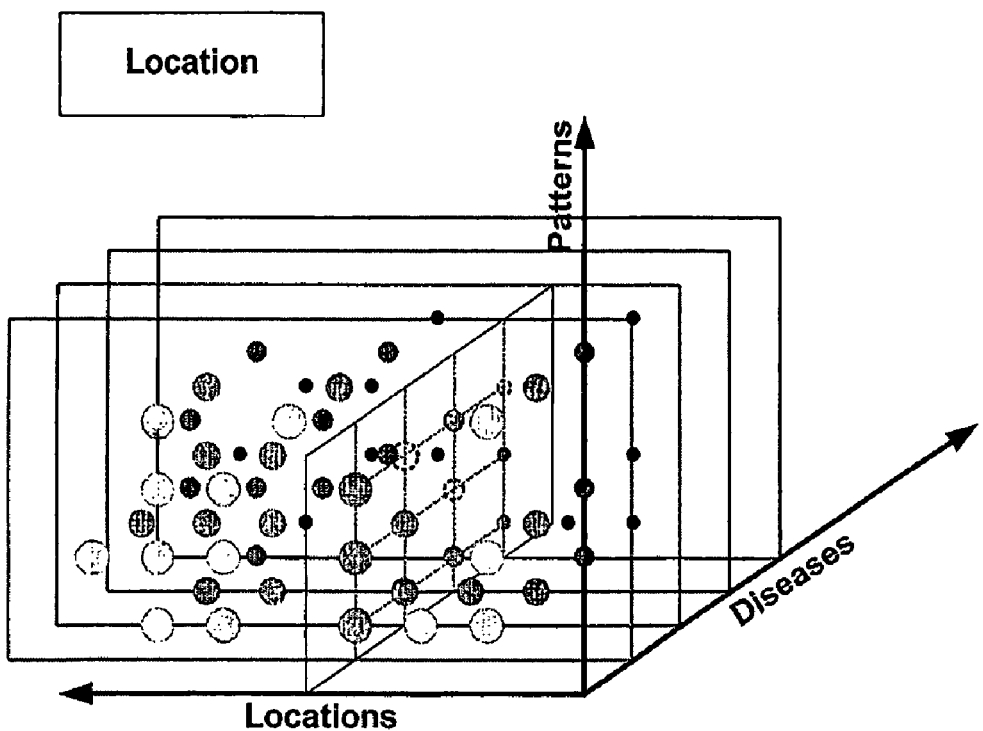
FIG. 6: Demonstration of the invention's work flow. The possible combinations of patterns and diseases for a given location are represented by the solid circles in the plane of the location. The empty circles correspond to combinations of patterns and diseases that do not occur in practice.

When the operator of the invention identifies the location of an abnormality, the invention is capable of providing a set of possible conditions. In FIG. 6, this is visualized as the solid circles on the mesh plane. This first step of knowing the location is similar to the actual working practice of the radiologist. However, under prior art, the radiologist would have to read all available documentation and find out whether there's a matching pattern for each possible condition at the location. That would include the diseases shown as the empty circles on the grey plane. It is not until the information has been read by the radiologist that the disease is classed as relevant or not relevant. The time spent on reading irrelevant documentation corresponds to lost time. The use of a multidimensional database immediately narrows the choices for the operator.

According to one embodiment of the invention, an operator provides the method or system with his choice of pattern and location of an abnormality on a medical image, and initiates a search of the multidimensional database, which returns a list of conditions. The search is performed by extracting data from an intersection of the pattern and location planes crossed by the pattern and the location of the abnormality. The data is extracted along the disease or condition axis.

Figure 7:
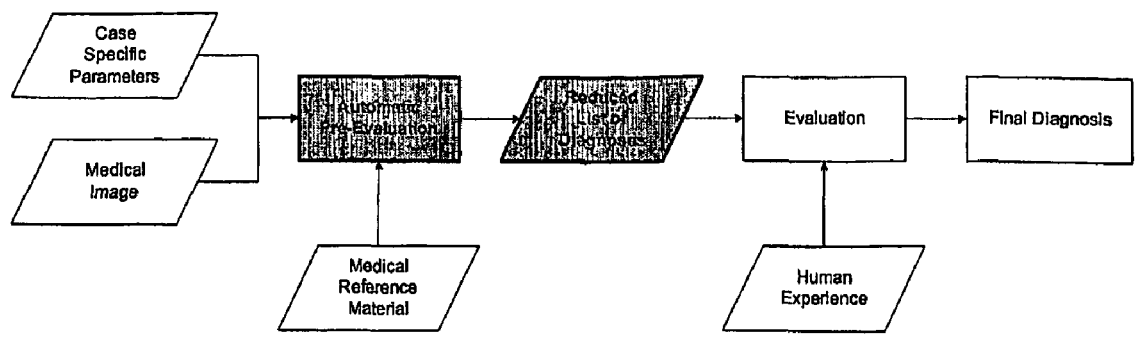
FIG. 7: Intended work flow for Radiological Care. Note the reduced dependency on Human Experience in this scheme.

Thus, the system and method of the invention can provide a list of one or more diagnoses which can assist in the diagnosis of a condition. As such, the operator can focus on a much smaller subset of possible diagnoses, and he will be less distracted by data not applicable to this particular case. Such steps of diagnosis are indicated in FIG. 7.

Figure 9:
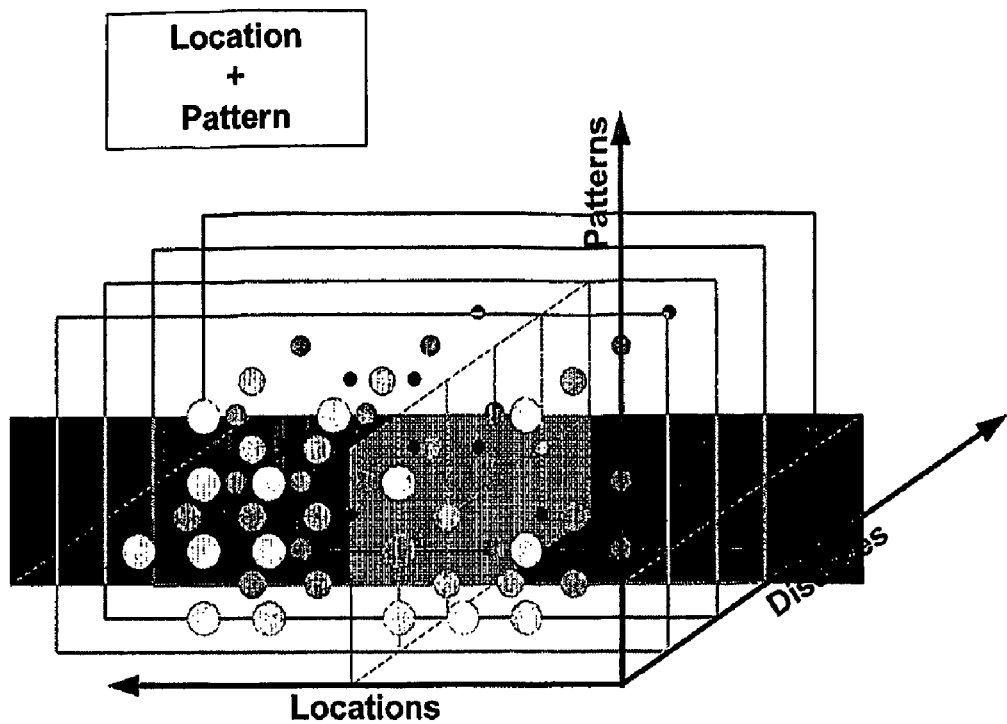
FIG. 9: Demonstration of the invention's work flow. The Radiologist first identifies the location, and the pattern from the medical image. Immediately, the set of possible diseases is reduced, as shown by the solid circles on the intersection between the planes for the given location and pattern.

FIG. 9 illustrates a mode of operating the invention whereby the operator specifies the location and the pattern of an abnormality. Identification of the location reduces the set of possible combinations to those lying in the vertical plane (shaded plane), while identification of the pattern reduces the set to those lying in the horizontal plane (cross-lined plane). The combination of location and pattern results in a reduced set of possible conditions, given by those diseases on the intersection of the two planes.

A further advantage of the multidimensional database is evident where simultaneous searching is performed of more than one abnormality. Once the operator has selected the patterns and locations of the abnormalities, the search is proceeded by extracting disease data from intersections of the pattern and location planes crossed by the patterns and the locations of the abnormalities. The diseases or conditions which are common to the patterns and locations, as well as diseases attributed to the each pattern and location are rapidly provided.

This feature is helpful in cases of rare conditions that present atypical imaging manifestations at two or more locations, and in which the combination of findings may provide a clue to the correct diagnosis. Using conventional methods, such diagnosis would require extensive cross-referencing of medical literature.

Figure 10:
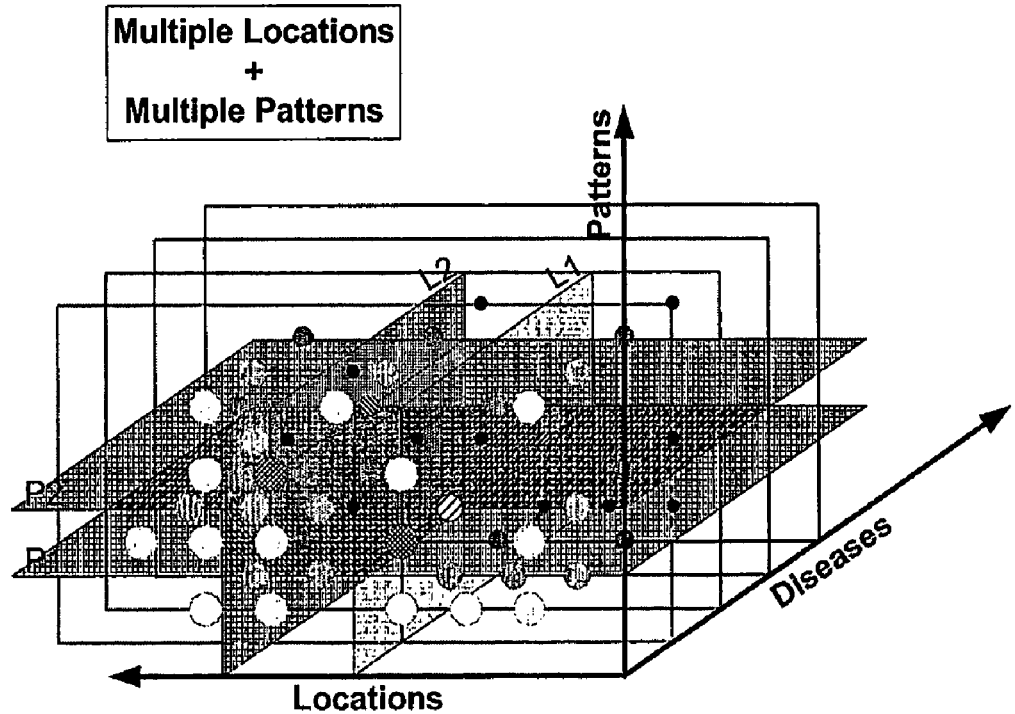
FIG. 10: Representation of a case with two patterns (P1 and P2) and locations (L1 and L2). The diagnosed disease is said to be shared amongst the patterns in question. This is shown as the two checked circles in the figure.

A mode of operating the invention in which two patterns and locations are searched is shown in FIG. 10. The operator identifies the locations, and the corresponding patterns. The first combination of a location and a pattern, L1 and P1, result in the set of diseases (the diagonally hatched circles) on the intersection of these planes. The second combination, shown (planes L2 and P2), result in another set of diseases (the dot-filled circles), on the intersection. These two sets of diseases have one disease in common, denoted as the check-filled circles in the figure. This condition will be presented to the operator or Radiologist as the most likely condition for the given input parameters.

Not only does the invention reduce the set of conditions to those diseases on the intersections between the two pattern planes and the location plane, a higher probability can be assigned to the disease that occurs for both patterns. The other diseases, corresponding to the dark hatched or dot-filled circles, each occur for only one pattern and location, and are less likely than this shared disease.

The multidimensional database may provide additional dimensions for the sex of patient, age, ethnicity, immune status and oncological antecedents, for example. The non-imaging data permits relationships between for example, ethnicity or immune status and the likely condition, to be determined. The non-imaging data may assist with ranking the diagnoses according to probability. For example, if it is known there is a predisposition to a type of liver cancer in men, such information may be used to increase the probability indication of the condition. The probability might be presented as a percentage, fraction, or be used to adjust the placing of the condition in an ordered list, for example.

The non-imaging information may also be used to request further information from the operator. For example, where non-imaging information has not been provided by the operator, and the database indicates a relationship between a likely condition and a non-imaging aspect such as age, for example, the system or method may request this information. Such information may be used to change the probability indication of the condition. The use of non-imaging information significantly improves the speed and accuracy of the diagnosis. The generation of long lists of possible diagnoses is avoided; normally such lists have to be refined by the operator and depends on the knowledge and experience of the operator. The use of non-imaging information allows precise questions to be formulated by the invention and provides focused diagnoses.

Ranking information is based on the frequency that a particular combination is encountered in practice, for a given combination of non-imaging parameters. According to an aspect of the invention, a default frequency may be provided. Exceptions to this default frequency are explicitly stored, together with the combination of the non-imaging parameters for which this exception occurs. The default rankings and exceptions may be defined by experts during the data entry process, based on their own experience and available literature data.

One embodiment of the present invention is a multidimensional database comprising medical imaging and optionally non-imaging data of subjects, wherein at least one dimension is provided for each of location, condition (or disease), and pattern of an abnormality, and optionally one or more dimensions provided for non-imaging data. As is understood in the art, the relational links between location and condition (or disease), pattern and optionally non-imaging data are provided in the database, so that the data can be represented and searched across data planes and intersections.

Figure 12:
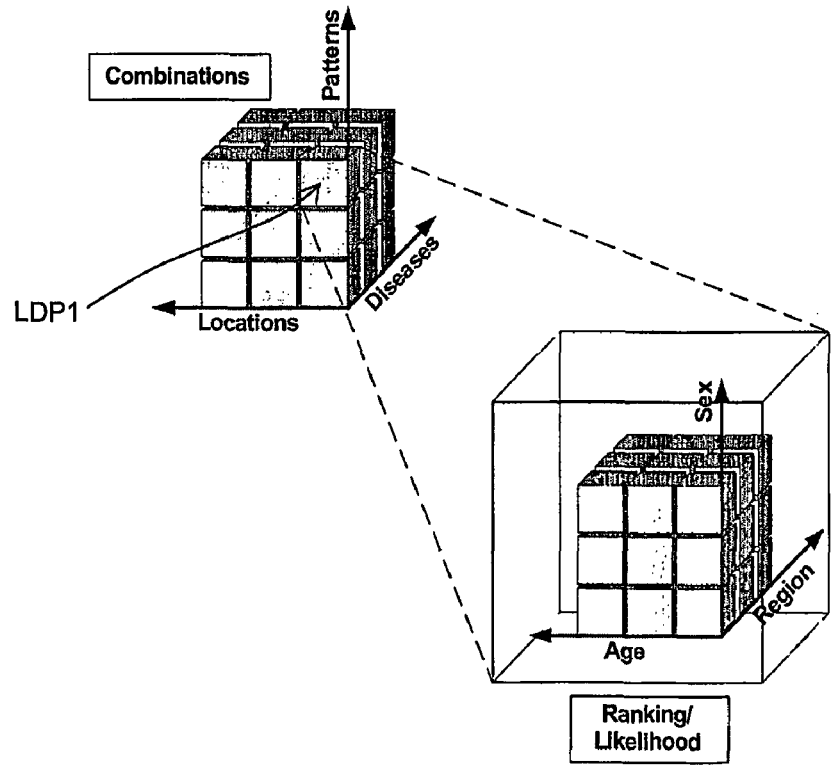
FIG. 12: Ternary relation between Locations, Patterns and Diseases. This relation is further specified using additional axes Age, Sex, Region. Other axes may be added if necessary.

An example of a multidimensional database is shown in FIG. 12. The upper left part of FIG. 12 indicates the combination of the location, pattern and disease visualized as a three-dimensional table or matrix. In the lower right part of FIG. 12 are additional dimensions containing non-imaging data associated with one particular location, pattern and disease (LDP1). Being a multidimensional database, the non-imaging data can be viewed as additional dimensions, and, as mentioned above, be used to rank a disease and/or prompt questions to the operator.

Figure 13:
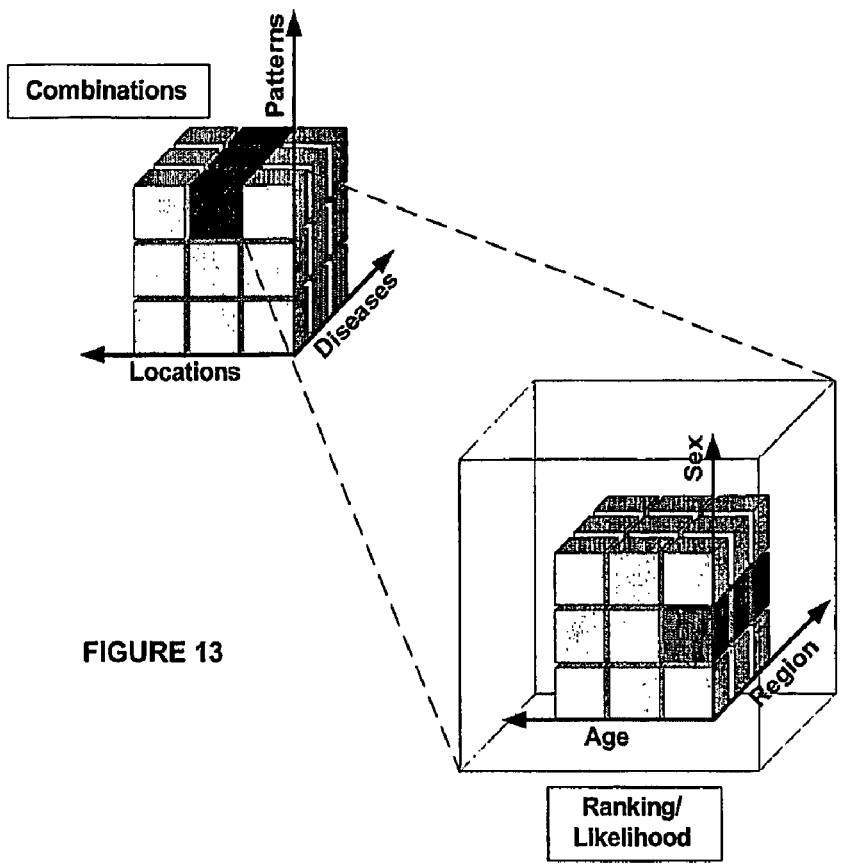
FIG. 13: Selection of input parameters corresponds to slicing the multi-dimensional table along the orthogonal axes. This is shown in the dark grey areas of the matrix.

Once an operator has chosen a pattern and location of an abnormality, he is presented with a list of possible diagnoses. FIG. 13 depicts schematically as cubes, three diseases (top left matrix, dark grey cubes) corresponding to the selected location and pattern. Each of said cubes is associated with further dimensions of age, sex and region (lower-right matrix).

Additional information such as age, sex and ethnicity may further influence the ranking of the diagnoses, and may even eliminate some diagnoses from the list. Alternatively, if the database indicates that ranking may depend on for example, age, the invention may prompt the operator to enter such relevant information. Therefrom, the probably or ranking of the disease can be established by the invention.

Figure 14:
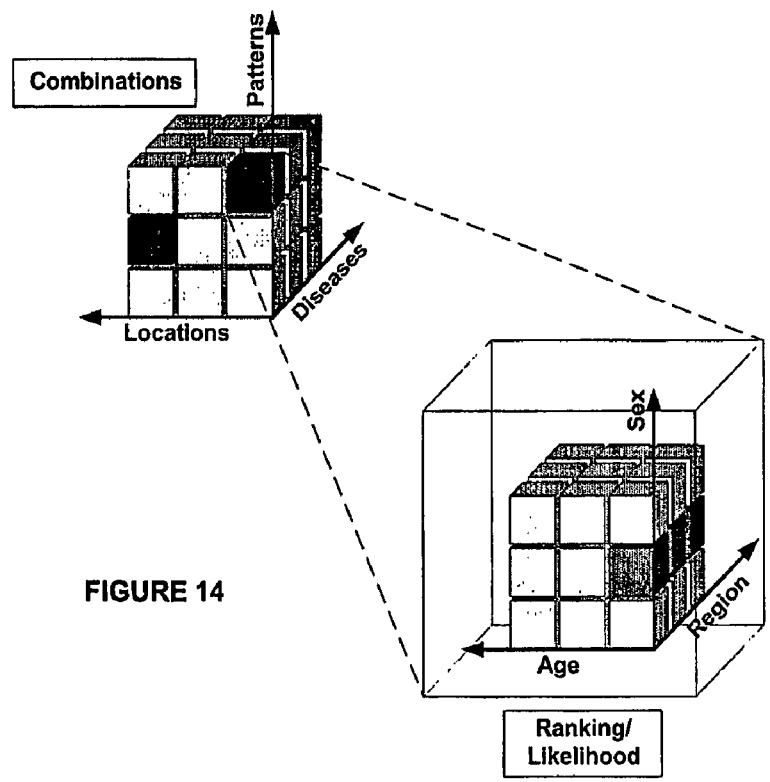
FIG. 14: Selection of multiple locations/patterns results in multiple slices, and as such more possible diseases. However, the system can automatically give a higher ranking to diseases reoccurring for the specified locations/patterns.

As previously discussed, the invention allows multiple patterns to be specified, and may automatically assign a higher ranking to those diseases shared by the given patterns. Such method is depicted schematically in FIG. 14. This shows a single diagnosis based on the input of two locations and patterns (top left matrix, dark grey cubes). Such diagnosis may also be given a ranking according any correlation between the patient data in respect of age, sex and region (bottom right matrix), as mentioned above.

According to an aspect of the invention, the database is not updated with continued use by the operator. Instead, the imaging and non-imaging data is provided only by experts, and is validated. This feature is described in more detail below.

The invention can also be used as a reference medium, comparable to the classical printed or online books. The operator has the possibility to browse the collected information, optionally according to location, pattern and/or disease, or non-imaging data.

Furthermore, the invention may be provided with a search engine, allowing the user to quickly find a particular item of interest, be it a location, pattern, disease, or other content.

Pattern/Location Discriminative Value

A further aspect of the invention is the use of a discriminative value for the combination of patterns and locations. Such value indicates to the method and system whether for the given location, a pattern is discriminative between diseases or is not. Such value is based on the proven significance of the patterns in making a diagnosis. For instance, a focal liver lesion is characterised by a limited number of patterns, of which the operator of the invention will be able to choose. If the operator unknowingly identifies a pattern which has low discriminative value, (e.g. "CT hypodense") he might receive the message that this pattern has a low discriminative value. The invention may then suggest a better approach (e.g. assess pattern of vascularisation). Alternatively, the invention may provide a list of diagnosis, in which the discriminative value is used as a factor to order the list by probability. Thus, by adding a discriminative value to the pattern dimension, a more accurate assistance with diagnosis is achieved. The database may thus comprise the discriminative value as a further feature of the combined location and pattern dimension. The discriminative value of a pattern at a particular location may be provided by the expert.

A system of the invention may be one or more device comprising at least one microprocessor capable of performing a method of the invention. The system may comprise at least one or two networked computers.

The operator of the invention may be a specialist or a non-specialist in the field of study. An example of an operator of the invention is a radiologist or a specialist in for example, cardiology, gynaecology, oncology, or other practitioner for whom interpretation of medical images is necessary.

Workflow of the Invention

Figure 11:
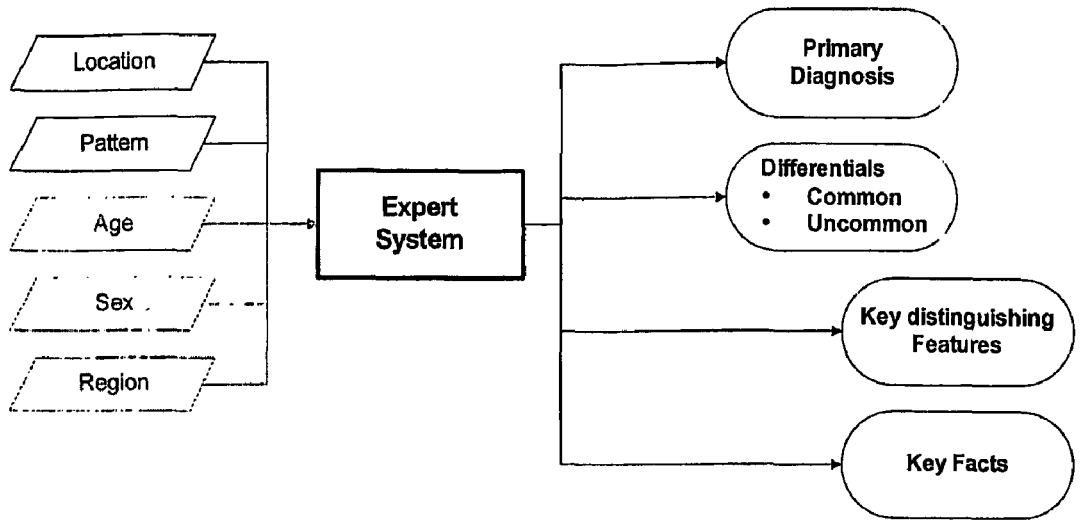
FIG. 11: The Expert System automatically presents a reduced list of diagnoses, ordered according to likelihood.

Confronted with a medical image, an operator of the invention identifies the location and the morphologic appearance (pattern) of an abnormality. All possible relevant combinations of locations and patterns are available in the database. The operator just has to select the appropriate location and pattern. As a result, he is given a focused set of diagnoses. Information on the likelihood of each diagnosis for this particular combination of location and pattern is also given. For some combinations of location and pattern, the system may indicate that additional input is required. Input of this additional (patient-related) information by the user results in an optimised ranking of the different diseases for that particular patient. The flow of input and output according to a method of the invention is shown in FIG. 11, in which the system performs a method of the invention.

Figure 45:
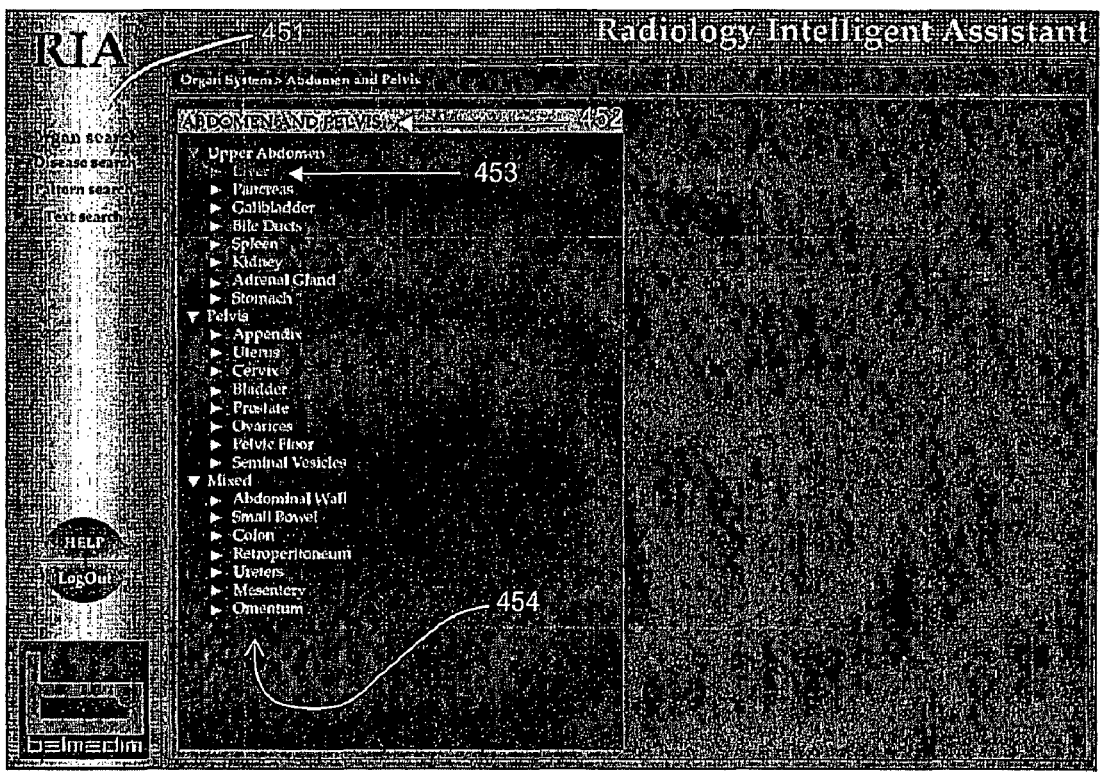
FIGS. 45 to 49: Examples of a radiologist user interface to the invention
Figure 46:
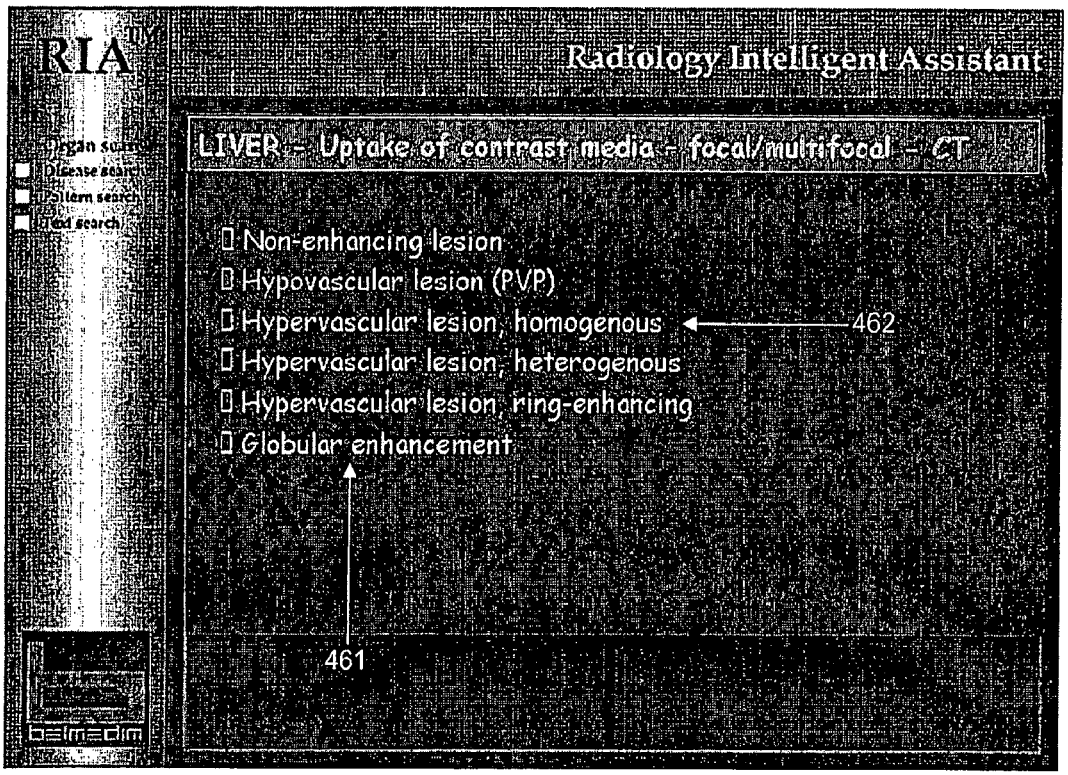
Figure 47:
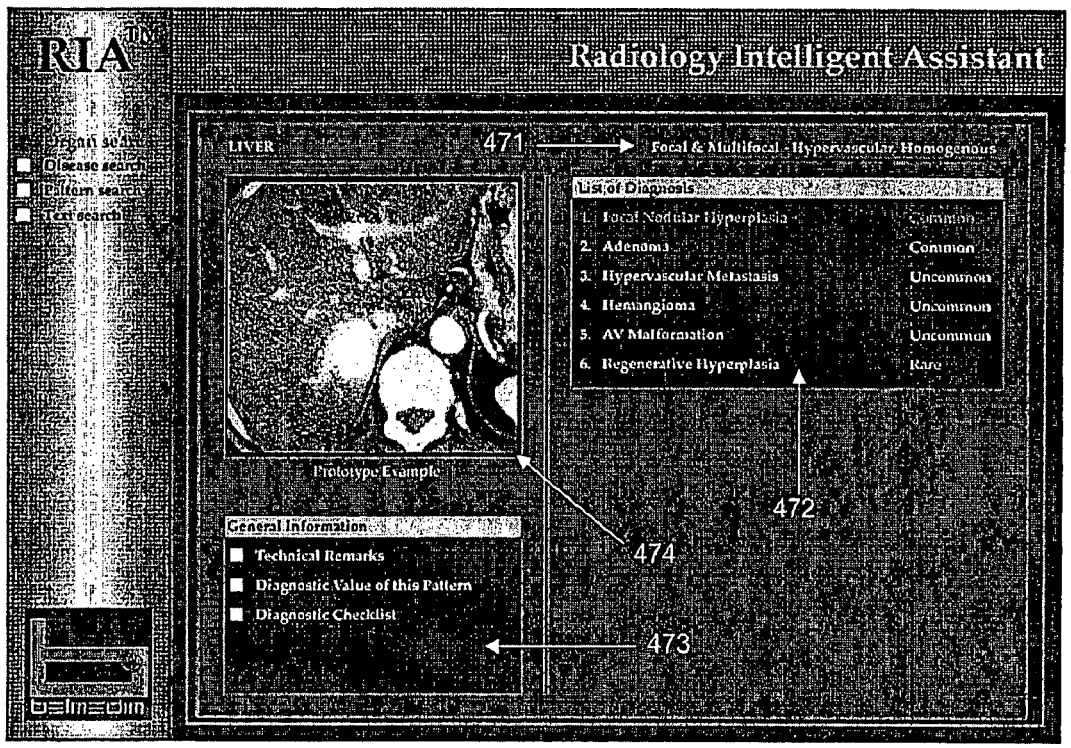
Figure 48:
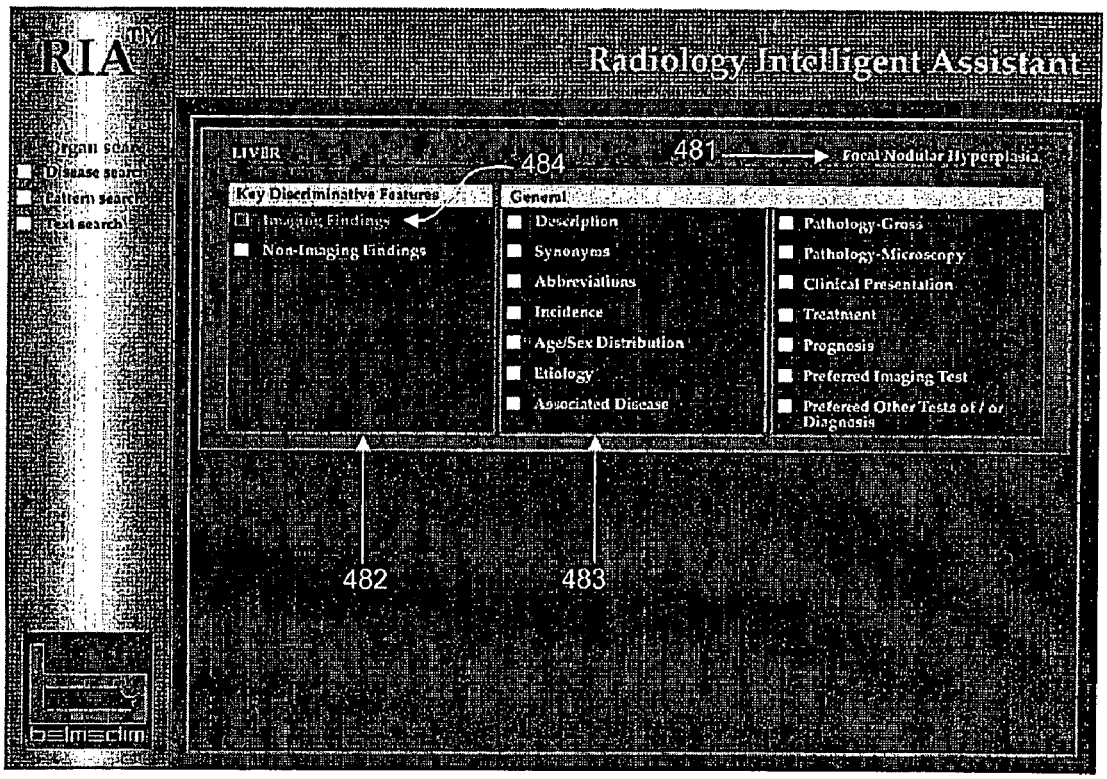
Figure 49:
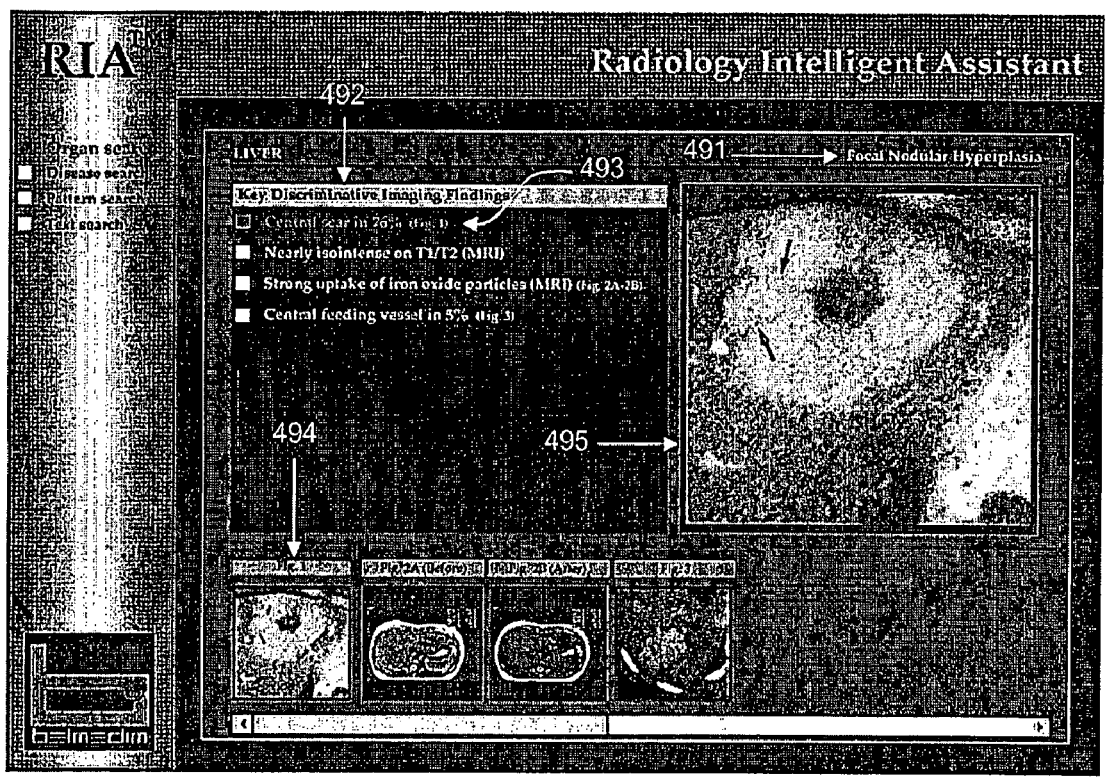

The operator can use the method of the present invention implemented into a computer program with a graphical user interface (GUI). A system comprising such interface is also known as a "Radiology Intelligent Assistant" (RIA™). With reference to FIGS. 45 to 49, the operator is presented with a GUI from which selections are available depending on he desired search. He can select a search of organs (locations), diseases, patterns or text (FIG. 45, 451). Already selected is the organ system of the abdomen and pelvis (452), from which a list of organs pertinent to each of the upper abdomen, pelvis and both of these is provided (454). In this case, the radiologist has selected Liver (453) as the location. The operator makes further selection of the category of pattern observed (e.g. morphological, contrast uptake, function), and selects 'contrast uptake', and further selects the technique (CT) and group 'focal and multifocal disease' (not shown). The focal/multifocal contrast uptake pattern in the liver observed by the operator can be identified from the lists of options (461) presented in FIG. 46, from which he selects 'hypervascular, homogenous' (462). Referring to FIG. 47, having selected a 'focal and multifocal—hypervascular, homogenous' pattern (471), the interface provides an image of a prototype example (474), a list of diagnoses (472) and general information (473) such as technical remarks, diagnostic values, and a checklist. In selecting the top ranking diagnosis, focal nodular hyperplasia, (481) the operator is presented with further selections in FIG. 48, such as key discriminative features (482) and general features (483). The first selection provides further information such as specific imaging findings, and specific non-imaging findings. In selecting 'imaging findings' (484), the GUI updates in FIG. 49 to display said key discriminative imaging findings (492). Each discriminative finding is listed, some of which are associated with an additional image. In selecting the first finding (493), the thumbnail image linked thereto (494) is enlarged (495). In performing the method of the invention, the operator is able to make an improved diagnosis of the disease attributable to the pattern observed. Compared to the currently available reference material, being a printed or online reference book, the operator does not have to carry the burden of reading lists of diagnoses, imaging findings, and other material that is irrelevant to the current case.

Furthermore, contrary to advanced types of reference material, such as search engines, the operator does not need to enter specific search criteria, that already assume a fixed idea about the resulting diagnosis. Instead, the system allows the operator to restrict himself to information that is readily available, and to postpone the interpretation to a later stage.

Integration

According to one aspect of the invention, the method or system is integrated within other systems, such as those with which the operator may already be familiar.

RIS/PACS and Other Applications

Currently, most radiologists work with Radiology Information Systems (RIS), Picture Archive and Communication Systems (PACS) or other computerized medical information systems. It is an aspect of the invention that the method, system and/or database has means to be integrated in these applications.

According to one embodiment of the invention, the method or system is provided with a number of standardized services and interfaces, that will allow the invention to be integrated with other applications. For example, an external application may send a message, containing the request, to the invention implemented as a computer program. The invention may respond with a message containing the result. Such message can be captured by the external application, and processed accordingly.

It is another aspect of the invention that the method is executed using a remote computer. Such arrangement permits remote requests to be processed, for example, over the internet, using a network and a central server, or any other remote/central server configuration.

It is also an aspect of the invention that the method may be integrated locally by providing a local instance of the content database (multidimensional database) and corresponding interfaces.

Speech Integration

According to another aspect of the invention, the invention is capable of communicating with an operator using speech or sounds. For example, the invention may recognize a vocabulary, and may be able to respond to the user. It may, for instance ask for more input, or provide the results of a particular operation.

Such speech integration may incorporate control and output of the operator's usual application (e.g. RIS, PACS or another medical information system), depending on the speech capabilities of this type of application. Such integration would result in a complete speech enabled work flow, so increasing the efficiency of the operator.

Lexical and Semantic Layers

As mentioned above, the vocabulary used in a certain medical area often contains several synonyms and different terminologies, while the data available in a content database often only contains a subset of the available vocabulary. An operator may not be able to understand the terms available for input or provided by an output, or may want to use a more familiar vocabulary.

According to an aspect of the invention, the invention incorporates the use of one or more lexicons. Such lexicons or semantic sources may be built-in or available as "plugs-ins", or as a file of translations, or any other means available to the skilled person. It is an aspect of the invention that such lexicon can be expanded by the operator, and/or that an operator can create their own vocabulary, and link it to the application. Such lexicon provides an advantage that search items can be compared with the available lexicons and semantic libraries. The method may then optimise the search criteria, and use the results from this lexical and semantic comparison as input for the search operation, in order to capture all relevant data. The output may also be translated according to the understanding of the operator.

This lexical layer integration is particularly useful for the more classical approach of the search engine.

External Resources

According to an aspect of the invention, the method of the invention may be capable of using data from sources other than the database. If such external resources are available, the invention may be linked to these resources to extend the information. Such external resources include conventional databases and multidimensional databases.

It goes without saying that the external sources should be subject to the highest quality criteria. Therefore, a validation of external sources is preferable, and it is even more preferable that external sources are certified.

The availability of external sources provides additional flexibility and extensibility to the invention. The invention may thus provide a central integration point for several databases, each built up by a independent providers or partners.

Input/Output Technologies

It is an aspect that the invention is capable of supporting at least one printed format and/or electronic display devices in order to indicate the diagnosis. Output may be provided in a non-interactive or interactive format. Non-interactive formats include the printed form as a book, brochure, or other paper formats. Other examples of non-interactive formats are static electronic information, such as a collection of linked HTML or XML pages, or using other publishing technologies, such as pdf (Portable Document Format). The number of available formats being unlimited; the data can always be converted into the appropriate format.

Interactive formats include the system being integrated in the end user's medical information system such as a RIS, PACS, or EMR (Electronic Medical Record).

The operator may interact with the invention using an interface. The interface may be incorporated into a web browser page, a proprietary interface, an interface generated using a database authoring tool etc. The devices providing at least the interface include a mobile phone, a PDA device, an organiser, a desktop computer, a terminal, a networked computer, a system comprising a microprocessor, an input device and a display device.

The application of these interactive formats is not limited by the output device. For the most common types of electronic devices, an application may be provided that offers a view to the system. These applications may be further speech enabled. A non-visual, speech enabled application can also be provided as a means to interact with the system.

Static database content may be installed locally. Provisions of sufficient disk space to store the content database are known to the skilled person.

On the other hand, static content may be made available via a web server. Provisions of networking (e.g. wired or wireless connection to an intranet or Internet, use of a web browser capable of working with the standard transfer protocols http and https etc) are known to the skilled person.

Dynamic, interactive content may be made available by the invention. Such dynamic content may be provided by way of a connection to the intranet or Internet, and the use of a web browser capable of working with the standard transfer protocols http and https.

According to an aspect of the invention, a method or system is capable of providing an interface for the purpose of browsing data from the multidimensional database. It may comprise means for extracting data according to the searching requests of the browsing user. The interface may permit graphical one, two or three dimensional representations of data, and means for the browsing user to navigate therethrough.

The system may be capable of providing a primarily textual online book edition of the database as mentioned below.

The system may be provided with a search engine allowing the user to specify a number of search criteria. The result set is presented to him, so he can interactively browse any of the results. This engine may be integrated with a Speech Recognition engine to aid the end user in entering the search criteria.

According to another embodiment, the user may be guided by a number of discriminative questions about the problem area which leads to a reduced set of answers, very closely related to the problem. Again, speech recognition may help the end user in answering the necessary questions.

Data Entry

Data Entry Process

As mentioned above, a database of the invention comprises all possible combinations of locations, patterns, and conditions to which specific attributes and more detailed information may be attached.

According to an aspect of the invention, the content is provided by a group of experts in image interpretation, that might include, for example Radiologists, assisted by medical doctors having specialised knowledge about particular diseases. To provide the highest quality, one or more experts from each location or location groups (e.g. liver, kidney, colon etc.) may provide information to and/or validate the database.

A problem with existing systems is that data entry is subjective and can depend on the understanding and language of the operator. Such variation between operators can lead to incorrect entries in the database. To solve this problem, the inventors have designed an interactive data entry application which guides the data entry operator. Such guidance may be by asking questions to the operator, the use of choice buttons, pull down menus, used such to limit and make consistent the input of the operator. By using such application, the content is entered in a consistent form, and the reuse of pre-existing data is maximized.

According to an aspect of the present invention, an interactive data entry application is organized according to the natural work flow, and to the natural relations between the entities in the database. The data entry operator identifies the location, optionally sub location, pattern, disease, or a combination thereof. The data entry user may add characteristic information towards any type of entity encountered. This characteristic information is divided into several categories, which further enhances the search capabilities of the invention.

The characteristic information can consist of short descriptions, long descriptions, figures, with or without captions. Additionally, references to official publications, if applicable, are stored together with the corresponding data. According to an aspect of the invention, the categories are configurable. If, at a certain moment, the operator is required to provide an additional characteristic, such characteristic may be added to the system.

To increase the productivity of the data entry users, the data entry application may be speech enabled. Additional interfaces may be provided for import of data in several structured formats (e.g. comma separated text, spreadsheets, XML documents). This interface may extend the solution to also input 3rd party data or data from remote data entry users.

Detailed Procedure of Data Entry

In order to create a database according to the present invention, the human body may be divided into basic anatomical locations. For each location, a radiology expert may be asked to create a comprehensive list of patterns and corresponding diagnoses. A standard template can be created such as shown in FIGS. 24 to 28 and used to enter this information. Note that the information gathered in the early stages may serve to create a structural backbone. Many more details concerning each location, pattern and disease may be added (together with information linked to specific combinations of a location and a pattern, a location and a disease, a pattern and a disease, and a location, a pattern, and a disease) once the basic structure has been defined.

Basic Patterns

In order to facilitate the task of the expert, a number of basic patterns may be created (see, for example Table 2). Specific types of patterns may be predefined for specific anatomical areas, e.g. bone, heart, hollow organs, lungs, solid organs. The expert may use any of these patterns they consider appropriate. They can also combine existing patterns, make patterns more detailed, or create new patterns if needed.

Defining Patterns

An expert may use his own case material of the organ that has been assigned to him. Alternatively, he can use a handbook or other reference materials providing a collection of pertinent images.

In order to work in an organised way, he may define patterns in the following order:

(a) patterns of morphology, examples of which include focal abnormalities (single or multiple), diffuse disease, and abnormal size & anatomy. The morphological pattern may be something too large or too small, something that is displaced, a lesion or argan with abnormal density, signal intensity or echogenicity, or other morphological patterns considered by the expert important to make a diagnosis.

(b) patterns of uptake of contrast media, subcategories of which include focal abnormalities (single or multiple), and diffuse disease. The pattern may be evident by the absence or presence of contrast enhancement, an uptake of a specific contrast media, a contrast enhancement pattern that is homogenous or heterogenous, by exhibiting an evolution of density or signal intensity over time, or other pattern of uptake considered by the expert important to make a diagnosis.

(c) other patterns, which include, for example, pattern of blood flow, patterns of muscular contraction, other Guidelines for Definition of Patterns.

According to an aspect of the invention, a pattern preferably has a limited list of corresponding diagnoses. Three to five diagnoses is most preferable.

In case a pattern has more than five corresponding diagnoses, the pattern may be modified in order to make it clinically more relevant and to reduce the list of diagnostic possibilities. Modifying a pattern may occur in two ways: by combining two different basic patterns (e.g. "hypervascular AND T2 hyperintense") into one, or by adding one or more details to a pattern (e.g. "hypervascular, homogenous"). Once the list of diseases has been reduced, the pattern may be used. In an example, a pattern "focal lesion, hypervascular" located in the liver, provides too many possible diagnoses. However, by defining the following patterns: "focal lesion—hypervascular, homogenous", "focal lesion—hypervascular, heterogenous", "focal lesion—hypervascular, ring enhancement", and "focal lesion—globular enhancement", which patterns cover all hypervascular lesions seen in practice, a more limited list of diagnoses is obtained for each. These lists can further be limited by making use of specific patient subgroups (see below).

If the list of diagnoses is sell too long, it may be an option to group diseases. For example, for the location "liver" and pattern "parenchymal calcifications", the disease group "granulomatous disease" can be used instead of using "sarcoidosis" and "tuberculosis" as separate diseases. Another arbitrary example: in the masticator space, all primary malignant diseases can be grouped and called "primary malignant soft tissue tumors" instead of mentioning "squamous cell carcinoma", "malignant fibrous histiocytoma", "fibrosarcoma", "osteosarcoma", and "rhabdomyosarcoma" as separate entities. By doing so, the output becomes shorter and more relevant. With such grouping, however, disease groups may only used when the diseases in the group have more or less the same clinical significance. For instance, it would not be wise to group all malignant tumors together, because metastases and lymphoma have a clearly different clinical significance, treatment, and prognosis.

If the list of diagnoses is still too long, the expert may assign the five most common diseases (see FIG. 27, 277) and just mention the name of the other possibilities below (2711).

In case a pattern corresponds to only one or two diagnoses, the possibility to integrate the pattern into a more general pattern can be considered. For example, the pattern "fatty lesion" in the liver has a very limited differential (mainly lipoma, myelolipoma, both very rare in the liver). In this case, it is probably more practical to define a pattern "fat-containing lesion" and to include lesions as angiomyolipoma, HCC fat fatty components, etc.

In general, patterns refer to single lesions, e.g. "ring-enhancing lesion". With respect to multiple lesions, the following situations may occur:

if the presence of multiple lesions implies that different diseases should be considered in the top five list of possible diagnoses, the multiple lesions may be defined as a separate pattern (e.g. "multiple ring-enhancing lesions")

if not, this pattern may be considered to be included in the corresponding pattern for a single lesion if there is some change in the relative likelihood of the diseases in the top five list of possible diagnoses, a variant pattern may be defined. For example: the pattern "multiple ring-enhancing lesions" in the liver can be defined as variant pattern of "ring-enhancing lesion" because the likelihood of abscess or metastases increases, although the list of diseases remains unchanged.

Variant patterns and their significance can be described as a brief entry in the template. If a pattern results in approximately the same differential diagnoses as a pattern already defined (and that has morphologic similarities) it may be mentioned as "variant pattern". See for example FIG. 28 (283). If, in comparison with a pattern already defined, the top five list of corresponding diseases contains new diseases, a new pattern should be defined.

A pattern location is normally the location where a pattern is actually seen, not the location where an expert knows the pattern comes from. For instance, an exouterine fibroma presenting as an adnexal mass corresponds to the pattern "solid lesion" at location adnexa (not uterus). Similarly, intrahepatic splenosis presents a sa focal liver lesion not as a splenic lesion, and should be indicated in the location liver, not spleen.

Specific Sublocations.

It is possible that some morphologic abnormalities have a different significance when observed at a specific sub-location within an organ, or that some abnormalities occur only in or close to a specific anatomical structure.

For example: a hypodense lesion adjacent to the falciform in the liver has a different significance than a hypodense lesion elsewhere in the liver (usually corresponding to focal steatosis)

In such a case, a specific sublocation can be defined (e.g. FIG. 27, 272). If the significance of a particular pattern is different in that specific sublocation, two patterns can be defined: a pattern "hypodense lesion" for the liver in general, and a pattern "hypodense lesion" for this specific sublocation.

If a certain pattern occurs only at a specific sublocation, it can be defined once and the name of the specific sublocation entered into the system (e.g. FIG. 27, 272).

It is an aspect of the invention that there is no limit on the number of sublocations that can be created, neither on their nature.

Specific Patient Groups (Non-Imaging Data)

In some cases, the list of diagnoses associated with a pattern depends on patient-specific parameters, such as age and sex. Other patient-related parameters that may be relevant in some cases are the oncologic antecedents (known primary tumor or not), the immune status (immune competent or not), and the geographical area where the patient lives. The possibility to define a specific patient subgroup is within the scope of the invention. For example, in FIG. 27 (273) the possibility is available to define a specific patient subgroup (e.g. child). If no specific subgroups are defined, the information is for an "average" adult patient without specific antecedents.

It is possible to add a specific patient subgroup to make a more focused and thus more clinically relevant differential diagnostic list whenever considered appropriate.

Examples of the different subgroups that can be defined can be found in Table 3 above.

The Number of Patterns to be Defined

Preferably an expert would define basic, new or combined patterns until all abnormalities found in his collection/practice or in books/journals fit in at least one pattern.

The expert would need to account that
the radiologist using the present invention to assist with a diagnosis may have images obtained either with US, CT, MRI, angiography, or conventional X-ray
an incomplete study may have been performed (e.g. unenhanced CT)

In all these cases, all abnormalities observed should fit "somewhere".

Entering the Information Using an Example Template

Figure 24:
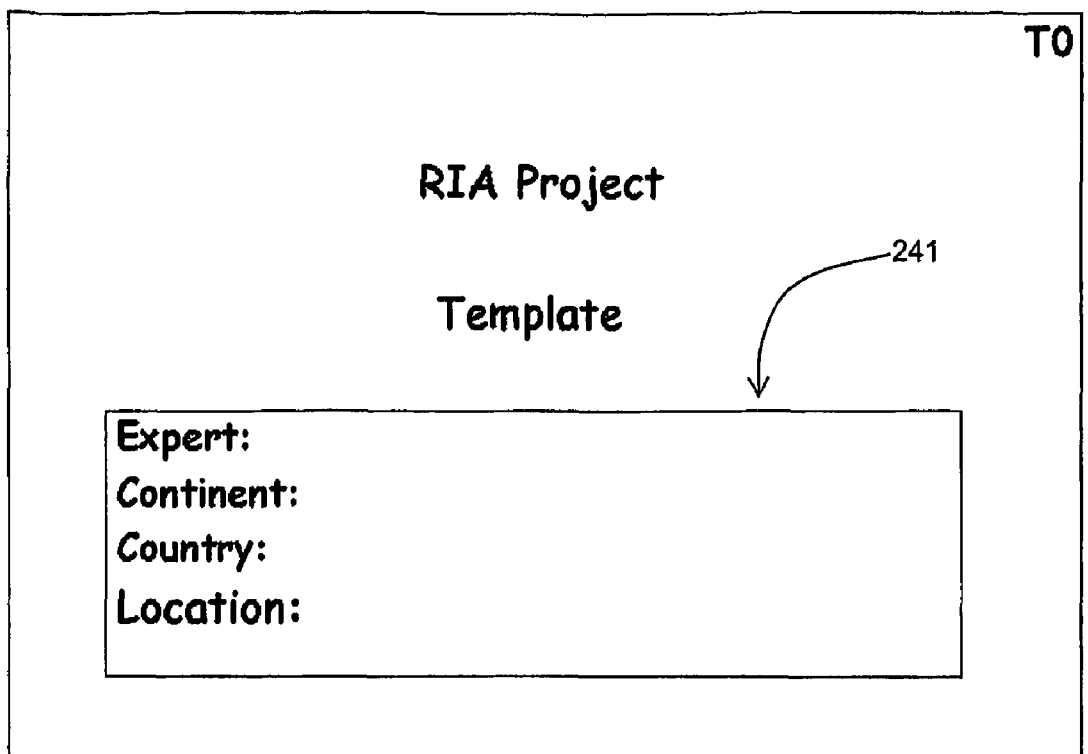
Figure 25:
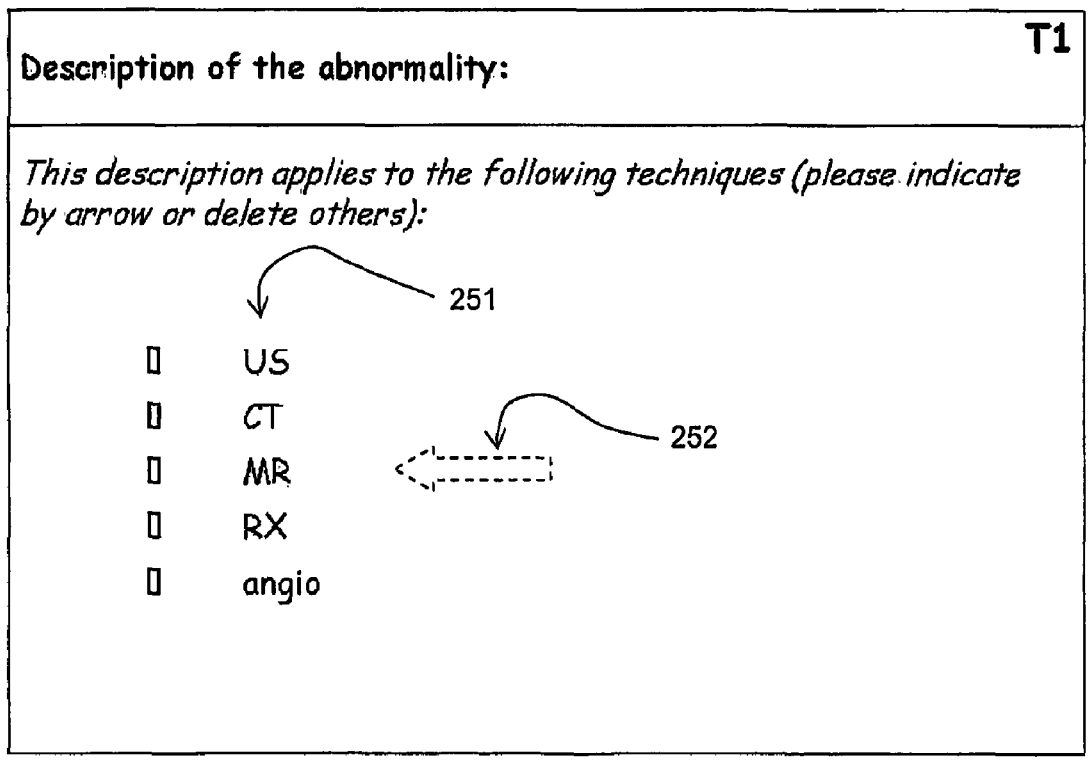

An expert may be provided with a blank template for data entry according to that shown in FIGS. 24 to 28, or equivalent which requests similar information from the expert. Data may be entered by the expert using the following steps, or equivalent steps thereof which provide the same data to the database:

STEP 1. The name of the expert, the continent in which he lives, the country therein and the body location assigned to him may be entered (FIG. 24, 241).

STEP 2. The technique used to detect the abnormality is indicated, for example, by the use of an arrow (FIG. 25, 252) against one of the list of applied techniques (251).

STEP 3. The type of pattern detected is indicated again by the use of an arrow (FIG. 26, 262) against one of the list of patterns (261).

STEP 4. A pattern may be entered (FIG. 27, 271). Optionally, if required, a specific sublocation (272) and/or a specific patient subgroup (273) are entered.

STEP 5. The diagnostic value of this pattern at this location and for this specific subgroup and sublocation—if any—may be chosen: high or low (274). The purpose of this item is to educate the reader/user by giving information about the clinical usefulness of the selected pattern.

High diagnostic value means that this pattern helps in making a clinically useful distinction between different diseases. Of course, the goal is to define the patterns in such a way that all patterns have a high diagnostic value but this is not always possible.

If 'low' is chosen, the pattern is a "pattern with low diagnostic value". In this case, the comment section (275) may be used to explain what should be done next (see also STEP 6). For example: Organ: liver; pattern: "focal lesion, hypodense (unenhanced CT)". In the section "comment" the following text may be inserted "additional imaging should be performed using either contrast-enhanced CT, US, and/or MRI".

STEP 6. A comment is entered if appropriate. Here (275) any comment can be entered by the expert. As mentioned above, if a low diagnostic value was assigned, the comment can suggest to look for another feature (e.g. pattern of vascularisation) or to obtain additional tests. Similarly, if the pattern has a high diagnostic value, the expert can also choose to give some comment on this (e.g. which diagnoses are unlikely).

The comment may also briefly mention technical requirements such as advanced equipment used or particular procedures needed. For example, a CT study of the coronary vessels may require a spiral CT with 64 slices. A technical requirement may be coded, for example "TR".

STEP 7. An example image may be added. This is an image (276) of an actual pattern and which typically illustrates this pattern.

STEP 8. The names of the diseases most commonly corresponding to this pattern may be entered, in decreasing order of likelihood (277). Typically, entry is provided for five diseases though more or less may be provided. Disease groups are also allowed such as granulomatous diseases, infectious diseases, metastatic diseases, viral pneumonia, mycotic infection (see also above). The disease stage may also be included in the entry (e.g. primary TB, post-primary TB, late-stage TB) as some diseases may have different imaging features during the evolution of the disease. If no hard data concerning the relative frequency of the different diseases as cause of a particular pattern is available, the experience of the expert can be called on. If the expert is unsure about the ranking (1 to 5), he may use his best guess.

STEP 9. If there are more than 5 possible diseases, the name of disease No 6 onwards may be entered in the field "other possible diseases" (2711).

STEP 10. In another column of the table, the likelihood that a disease causes the defined pattern may be entered (278).

For disease number 1, there is only one possibility: per definition, this disease is the primary diagnosis.

For disease Nos: 2 to 5, a choice can be made between "common" or "uncommon"
  common: "to be expected" a diagnosis you expect when you observe this pattern
  uncommon: possible but not suspected It is an aspect of the invention that an expert can use percentages or other indicators instead of or as well as the words "common" or "uncommon".

STEP 11. In another column of the table, the likelihood that a disease present with the pattern defined may be described (279).

There may be two possibilities:
  typical: "to be expected" a pattern you expect when know the underlying disease
  atypical: not what you expect for this disease It is an aspect of the invention that an expert can use percentages or other indicators instead of or as well as the words "common" or "uncommon".

Note that step 10 is different from step 11: a different type of question is answered:
  step 10: a pattern is observed, and the expert must consider how likely a particular disease is
  step 11: a patient presents with a particular disease, and the expert must consider how likely is a particular pattern.

The difference relates to the prevalence of different diseases. Consider a very common disease (disease No 1) and a very rare disease (disease No 2). A particular pattern may be typical for both diseases ('typical' in step 11). At the same time, disease No 1 can be a common cause of that pattern, while disease No 2 is an uncommon cause (simply because it is such a rare disease).

STEP 12. Key discriminative findings may be entered. These are defined as specific imaging and non-imaging findings that allow this disease to be differentiated from other diseases at the same location and with the same pattern (2710). A brief summary of the frequency and precise significance of these findings (if any) may be entered. Preferably a unique number to each of the key discriminative imaging findings is assigned. For example, example: liver, focal lesion, hypervascular and homogenous—FNH: central scar (not obligate), strong uptake of iron oxide particles, sometimes central feeding artery, usually iso- or hyperdense in portal venous phase.

Figure 28:
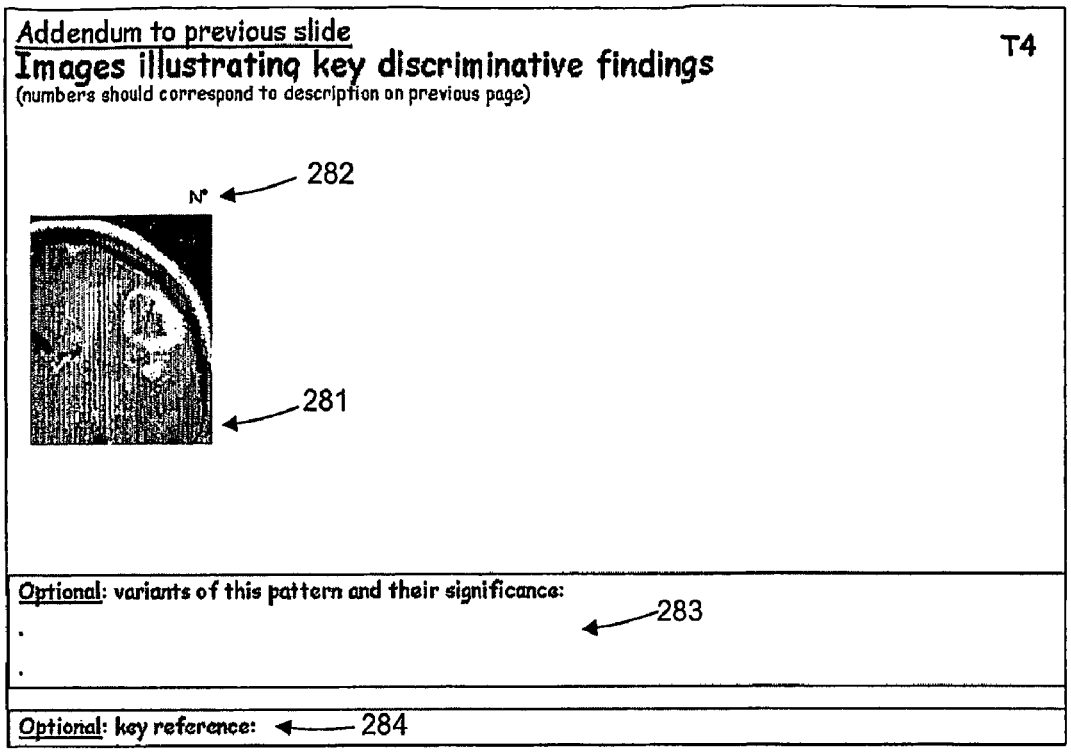
Figure 29:
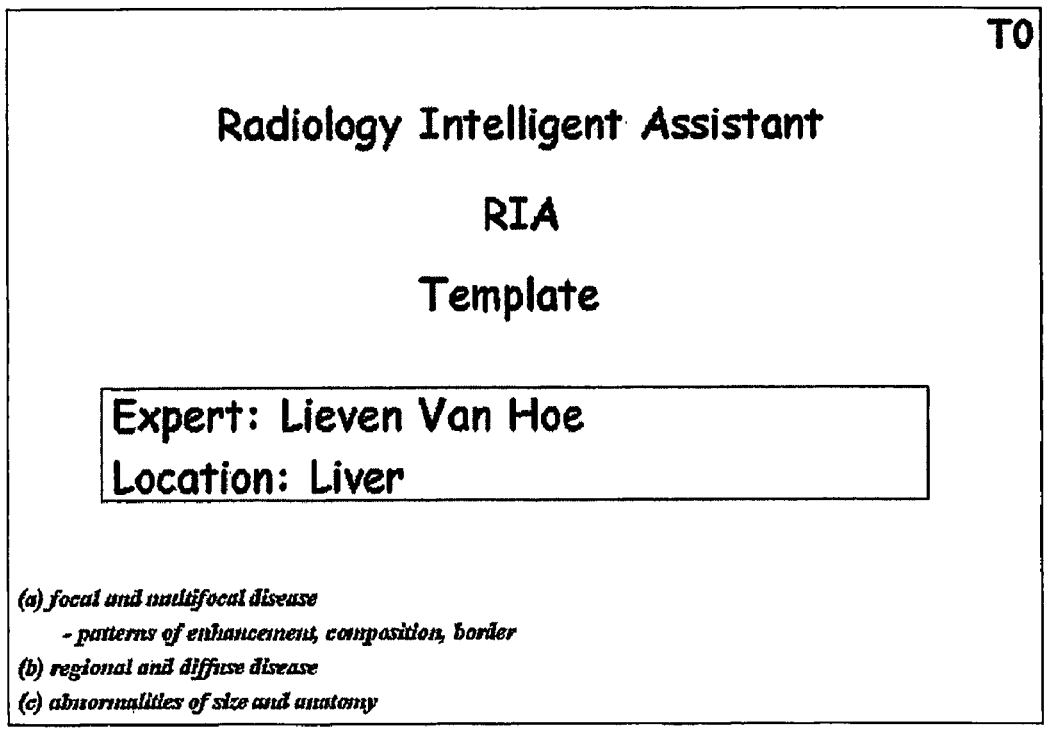

For each key discriminative imaging finding, a typical example (e.g. one or several images) may be provided (FIG. 28). A number (282) should be placed on the images (281) identifying the finding.

If considered appropriate, information about technique (e.g. T2 weighted image, TE=360 msec) or final diagnosis can be added.

If there are several key discriminative findings to be illustrated, an extra copy of template can be made.

STEP 13: Variants of this pattern and their significance (if appropriate) can be briefly described (283). In some cases, variants of a pattern result in a slightly modified differential diagnosis. In this case, rather than defining a new pattern, the variant can be described and its significance (e.g. FIG. 28, 283, as discussed above).

Figure 30:
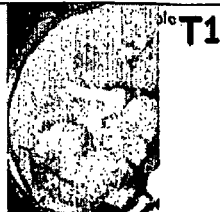
Figure 31:
Figure 36:
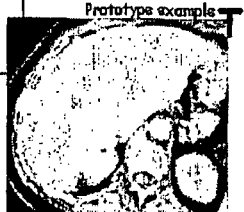
Figure 37:
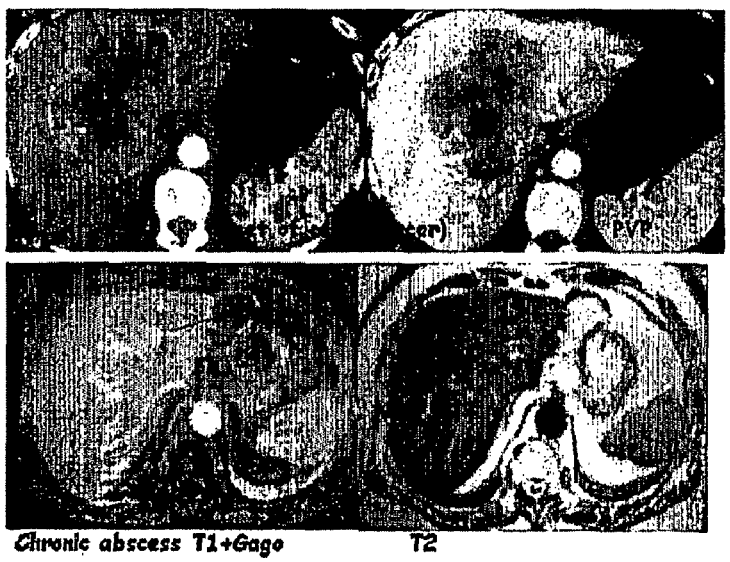
Figure 38:
Figure 39:

STEP 14: One or more images illustrating key discriminative features is provided by the expert (FIG. 28, 281), preferably referenced (282) to a number in the previous slide. For example, in FIG. 30, two reference signs (301) find corresponding images in the addendum (FIG. 31, 311). If needed to avoid confusion, specific diagnosis or technical details can be mentioned as a legend to the figures(s).

STEP 15. Selected key references can optionally be provided (284).

All the information may be stored in a central database. This database may be open for continuous updating and refinement by the experts. Thus mistakes can be corrected at a later stage.

Selection from Predefined Lists, or Free Input

The expert, as well as the radiologist, can select input from predefined lists. Examples of selections from which the expert may choose include for example, location, type of abnormality (category), imaging technique corresponding to a description, possible patient subgroups, common/uncommon (step 10), typical/atypical (step 11). Aside from the predefined choices, the expert may also freely define other inputs such as, for example, definition of sublocations, definition of patterns, technical requirements of an imaging technique, key discriminative features, images, comments, and variant patterns.

Examples of Completed Templates

Examples of templates partially of fully completed by an expert in accordance with the invention are depicted in FIGS. 29 to 43.

Figure 44:
FIG. 44: Example of a page of a book or output provided by the invention

According to an aspect of the invention, a product will be a series of books. In this series, one page may be assigned to each pattern (see example page in FIG. 44).

Validation and Approval

It is an aspect of the invention the system is configured to prevent data being published, either interactively or non-interactively, without specific approval of dedicated Validation users and Approvers. Validation users and Approvers may be different from the data entry users who are responsible for entering the bulk of the data into the database'.

Such configuration may allow every data item to be checked before it is released as publishable data. To increase the productivity, the user responsible for validation and/or approval of the data, may be presented a list of non-validated modifications.

Navigation System

One aspect of the invention is a system for navigating a multidimensional medical database as mentioned herein. The system comprises a means for accessing a multidimensional database, a means for inputting navigational information, and means for extracting from the multidimensional database a list of conditions, patterns, locations depending on the navigational information.

The system may provide navigation tools including interactive displays which make use of alphanumerical characters and graphics to represent the data.

The information contained within the system can be browsed along several axes, depending on the known input parameters. The most natural work flow is to provide input about the location and the pattern, but the system will also allow to be browsed as an encyclopaedia for information related to locations or patterns in case the disease is known.

According to an aspect of the invention, a navigation system comprises means to providing results of navigation as one or more of text, numbers, case examples, drawings, computer generated graphics, video clips, or any other type of relevant output.

The methods or systems of the invention may be provided as a computer program held on a computer readable medium, said program comprising computer code for performing the steps of the method or for providing the functionality of the system. Examples of media include an optical disk, tape, magnetic disk, solid-state memory, hard-drive. The program or system may be available for download across a network.

According to one aspect of the invention a method or system is implemented into a stand-alone system, for example, as a package on a desktop computer with a screen and input device, on a laptop computer, on a PDA etc.

One embodiment of the invention is a device capable of performing a method of the invention.

According to one aspect of the invention the database may be present on a remote server and a program present on a networked local computer to provide an operator with an interface for interacting with the database. Such interface may by provided by known technologies, for example, displayed in a web page, a proprietary interface, an interface generated using an authoring tool etc.

The invention includes any technology which permits the operator to interact with the invention. According to one aspect of the invention, the invention is capable of displaying a web page on a remote computer. Said web page permits the operator to use the invention. It is an aspect of the invention that the use of the method or system by the operator is recorded by the invention for the purpose of billing the operator or his employer. Such billing systems are known in the art. For example, the invention may provide each operator with an account which is charged according to the use of the invention. Such charging may be according to time, the number of searches, complexity of searched, volume of data transfer, or by license with privilege options, etc.

Another aspect of the invention is a multidimensional database product as described above. The database is preferably curated by a team of experts in pattern recognition. As already mentioned above the database is multidimensional, comprises at least three dimensions, with location, pattern and condition data being stored in least one dimension each. Non-imaging data comprising the sex of patient, age, ethnicity, immune status and oncological antecedents, for example, may be provided in additional dimensions. The database comprises all possible combinations of locations, patterns and conditions to which specific attributes and more detailed information are attached.

According to an aspect of the invention, a database product is capable of providing or interacting with an interface for the purpose of browsing data from the multidimensional database. The interface may comprise means for extracting data according to the searching requests of the browsing user. The interface may permit graphical one, two or three dimensional representations of data, and means for the browsing user to navigate therethrough. The database may be capable of providing a primarily textual online book edition of the database as mentioned below.

The database product may be provided with a search engine allowing the user to specify a number of search criteria. The result set is presented to him, so he can interactively browse any of the results. This engine may be integrated with a Speech Recognition engine to aid the end user in entering the search criteria.

According to another embodiment, the database user may be guided by a number of discriminative questions about the problem area which leads to a reduced set of answers, very closely related to the problem. Again, speech recognition may help the end user in answering the necessary questions.

One embodiment of the invention is a device comprising the database product or capable of accessing the database product.

The features of the database product mentioned above are not limited to the multidimensional database product, but may also be integrated to the system or method of the invention.

The multidimensional database product may be provided as a computer program held on a computer readable medium. Examples of media include an optical disk, tape, magnetic disk, solid-state memory, hard-drive. The database program or system may be available for download across a network. It may be available under licence or pay-per-use.

The present invention closely follows the natural work flow of the Radiologist or medical specialist. Contrary to the current state-of-the-art, the invention allows a considerable reduction in the need for manual intervention, by making an automatic pre-selection based on a number of well-known measurable parameters. As such, the invention facilitates and improves radiology work flow, i.e. the extraction of relevant information from medical images.

The invention is structured around a multi-dimensional relationship between location, pattern and disease, and shows further dimensions according to case specific parameters such as age, sex and geographical region. This allows a business intelligence like approach to a content database.

The use of patterns as one of the primary navigation axes, offers completely new insight in medical reference material.

Furthermore, the introduction of a ranking of diseases for a particular set of input parameters helps to increase the quality of the diagnoses.

Figure 20:
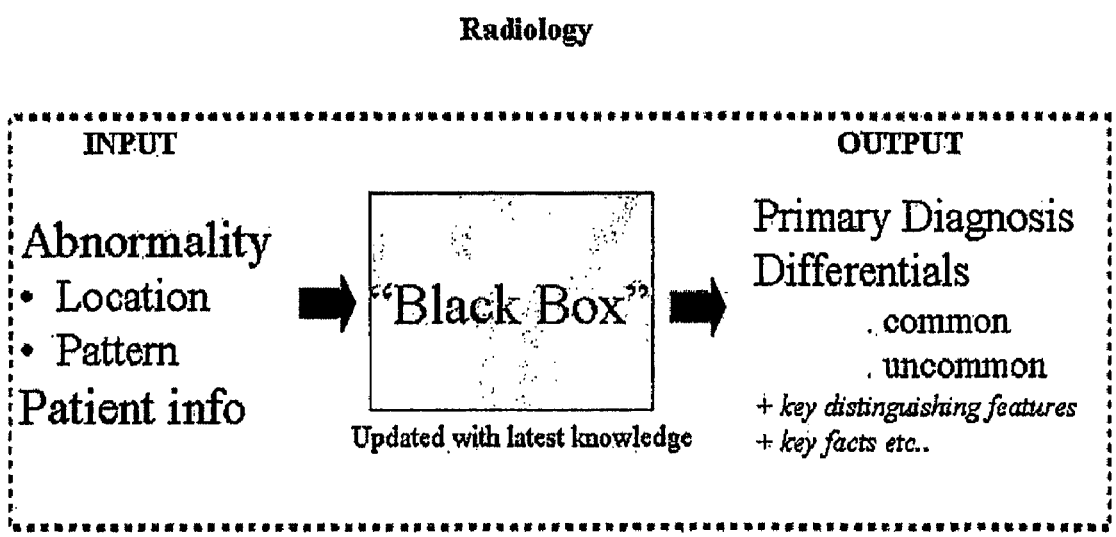
FIG. 20: The invention relates to the extraction of key parameters out of images and providing these parameters (together with other relevant data such as patient information) to the "black box". The "black box" is designed to convert this information to a clinically relevant output.

Importantly, the invention enables the user to obtain relevant information after having identified some basic parameters such as Location and Pattern. As such, the invention covers process that enables the transformation of images to diagnoses, and the technical structure of the system is irrelevant to the operator. This is illustrated in FIG. 20, where the database/system is indicated as "black box", the functioning of which the operator is unconcerned.

EXAMPLES

The above mentioned embodiments may be implemented using techniques known in the art. The architecture described below represents only a few ways of implementing the method, and the invention is not limited thereto.

Example 1

Basic Concept

The system of the invention has been designed to facilitate and improve natural work flow of the operator. Although the operator is sometimes referred to as a radiologist, such professional can be any involved in the process of diagnosing a condition on the basis of medical image data.

System Architecture

Figure 15:
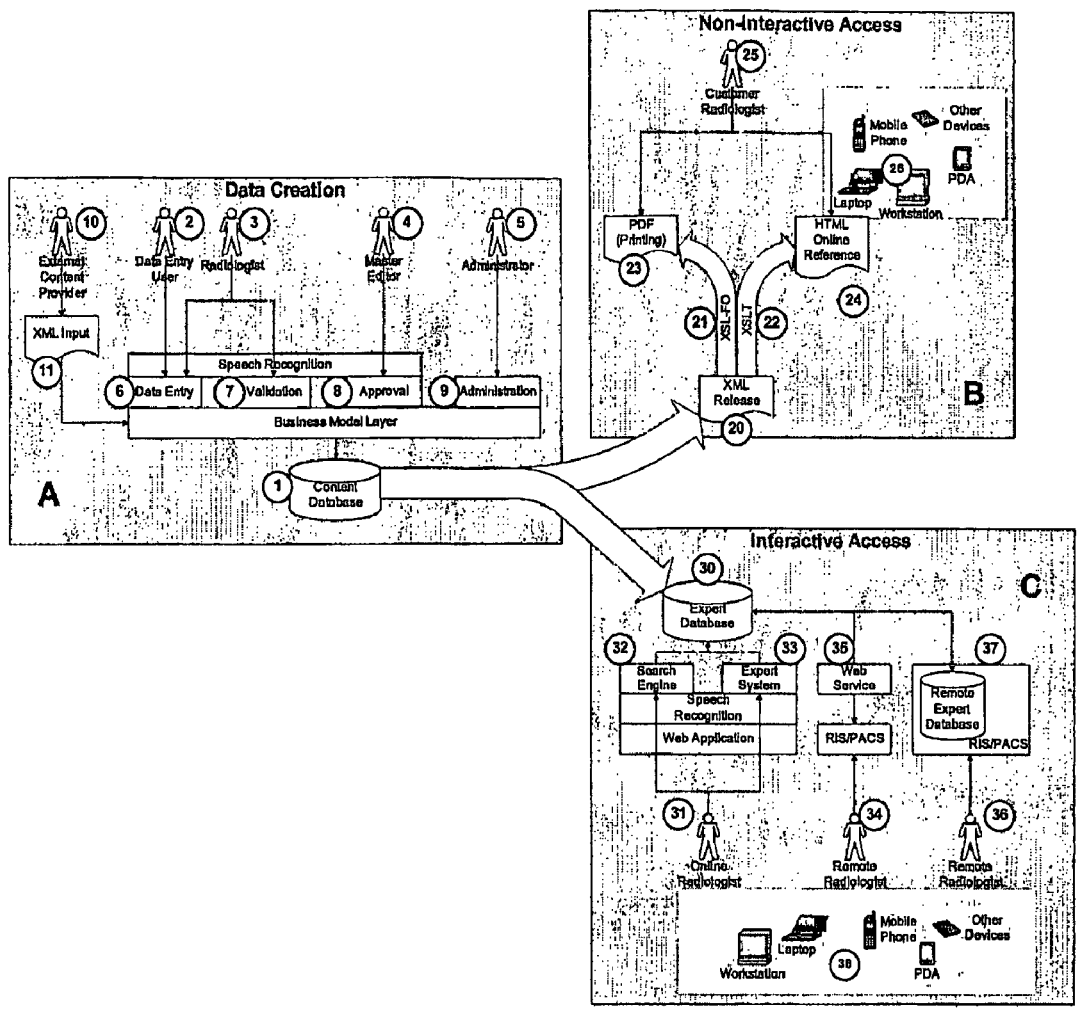
FIG. 15: System Architecture and major process flows

According to one embodiment of the invention, the architecture of the system of the invention is shown in FIG. 15 which is elaborated below.

Data Creation (A)

This part of the architecture adds content to the database (1). It is preferably located at the site of the data producer. Preferably, no external operators (i.e. not contractually linked to the producer) would be allowed in this environment. Several roles can be defined, each of which are discussed below.

Data Entry User (2)

A non-specialist may be dedicated to entering pre-defined sources into the database, via the Data Entry module (6) in the Data Creation environment. As this user is not necessarily skilled in the domain of Radiology, the data entered should preferably be validated by a specialist. Although validation is still another step, the Data Entry operator can be responsible for the bulk import of much of the data.

Radiologist (3)

As an expert in the domain, a radiologist may have the same access privileges as a Data Entry operator, but may also allowed to check and validate (7) the data.

Master Editor (4)

As an additional role, final validation and approval (8) may be the privilege of an editor or project supervisor. This ensures the high quality of the database content, as any data element is subjected to multiple quality controls.

Administrator (5)

This user may be responsible for the definition of new users, assigning access rights, and for the creation of new categories, and for other administrative tasks using a specific Administrative Module (9), that, for reasons of security, may not be accessible to other Data Entry users or Radiologists.

All operations performed by any of these roles, may access the database through a common Business Model layer. This layer makes sure that the data remain consistent, even after multiple modifications.

In case of Data Entry and Validation, the user may be assisted by a Speech Recognition Engine, both for entering data into text fields, and for navigating through the pages.

External Content Provider (10)

Besides the regular forms of data entry and validation, an External Content Provider (10) may provide data. Such data may be wrapped in a well-known format, e.g. XML (11), which is automatically integrated, using the same Business Logic, into the Content Database.

The data creation process may be followed by a release or publication process. Different types of publications can be thought of, which we can be categorized into two parts. Non-interactive Access refers to fixed layout, while Interactive Access refers to dynamically changing representations of the data. This is explained in more detail in the next paragraphs.

Non-Interactive Access (B)

The most common form of non-interactive data access is a printed book (23). Because this is currently still the most popular option, it is an aspect of the invention to provide content for publications in printed format (23) or related formats such as, for example, in the pdf format.

There may also be an online book edition of the database (24). According to one example, users can obtain a license that allows them to browse online a number of books published using content provided by the invention. Advantages of this type of access are updates of the database can be part of the license. An online user will be guaranteed to browse the most recent content release.

the user may switch between several books on his personal bookshelf, with possibly a maximum number of switches per fixed period.

In books, the data remains static, and search operations can only be performed by using an index, or by extensively navigating through the web site.

Other possibilities are to publish the database in a well-known format, such as pdf. The disadvantage of this approach is that pdf documents can be easily be shared between users, allowing license agreements to be bypassed. Therefore, formats which allow a licence provider to determine the lifetime of the readability of the format are preferred.

In order to provide these static forms of publications, the database content can be translated, at regular release times, into XML format (20). The XML document may be then further processed, via XSL-FO (21) into pdf, which can be used to create a printed book.

On the other hand, the XML document can be split-up, using an XSLT-style sheet (22) into several linked static html pages, to serve as an online publication of the material. Using the same technique, these html pages may be served to several electronic devices such as Workstations, Laptops, PDAs, mobile phones, or other devices (26).

Interactive Access (C)

Interactive access can add value to the information provided by the method compared to the static resources. Different forms of interactive access are supported by the invention, each of which requires the release of the Content database (1) to an Expert Database (30). This is a copy of the database, in which some technical attributes for monitoring modifications are omitted. Furthermore, the Expert Database may contain several versions, depending on the licensing model.

Search Engine (32)

This type of application allows the operator user, a Radiologist (31) or specialist in another medical discipline with online access to the content database, to specify a number of search criteria. The result set is presented to him, so he can interactively browse any of the results.

This engine may be integrated with a Speech Recognition engine to aid the end user in entering the search criteria.

Expert System (33)

In this more advanced form, the end user (31) is guided by a number of discriminative questions about the problem area (based on the natural work flow navigation Location, Pattern, Disease), which leads to a reduced set of answers, very closely related to the problem. Again, speech recognition may help the end user in answering the necessary questions.

Remotely Integrated Expert System

This is a more advanced form, where the expert system (30, 35) is integrated remotely with the end user's application such as a RIS or PACS system (34) shown in FIG. 15. It should be noted that integration is by no means limited to RIS or PACS applications, and could be any medical information system. In the example of FIG. 15, the Expert System (30, 35) resides at the producers site, while the medical information system such as RIS or PACS is available at the end user's site.

Within the end user's application, the necessary search criteria are set up, and sent to the producer's site, where a web service (35) listens to the incoming calls, and returns the appropriate answers to the questions.

For security reasons, the connection between the remote site, and the producer's site, may be implemented as a VPN, or using secure socket layer technology (https).

Locally Integrated Expert System

In cases where a continuous online connection with the content database is inappropriate, a secured copy of the database (37) may be provided to the end user (36). The integration between the end user's application and the expert system is implemented locally, although the same techniques may be used (the producer providing a web service interface). Again, in FIG. 15 we have used the example of a RIS or PACS application, but the solution is by no means limited to these applications.

Display Devices

All presented solutions may be made available on a number of devices, including workstations, laptops, but also handheld devices such as PDAs and mobile phones. There is preferably a co-operative link to the Expert Database. Such link may be remotely made (e.g. via cables, across a network, or the internet, wireless link) or such database may be integrated into the device.

The technology is not limited to currently available electronic devices. Future electronic devices that may appear on the market, that for example, allow a connection to be made to the Intranet or internet, and are able to display web based content, are appropriate to act as a display device for the invention's content.

Example 2

Process Flow

Figure 16:
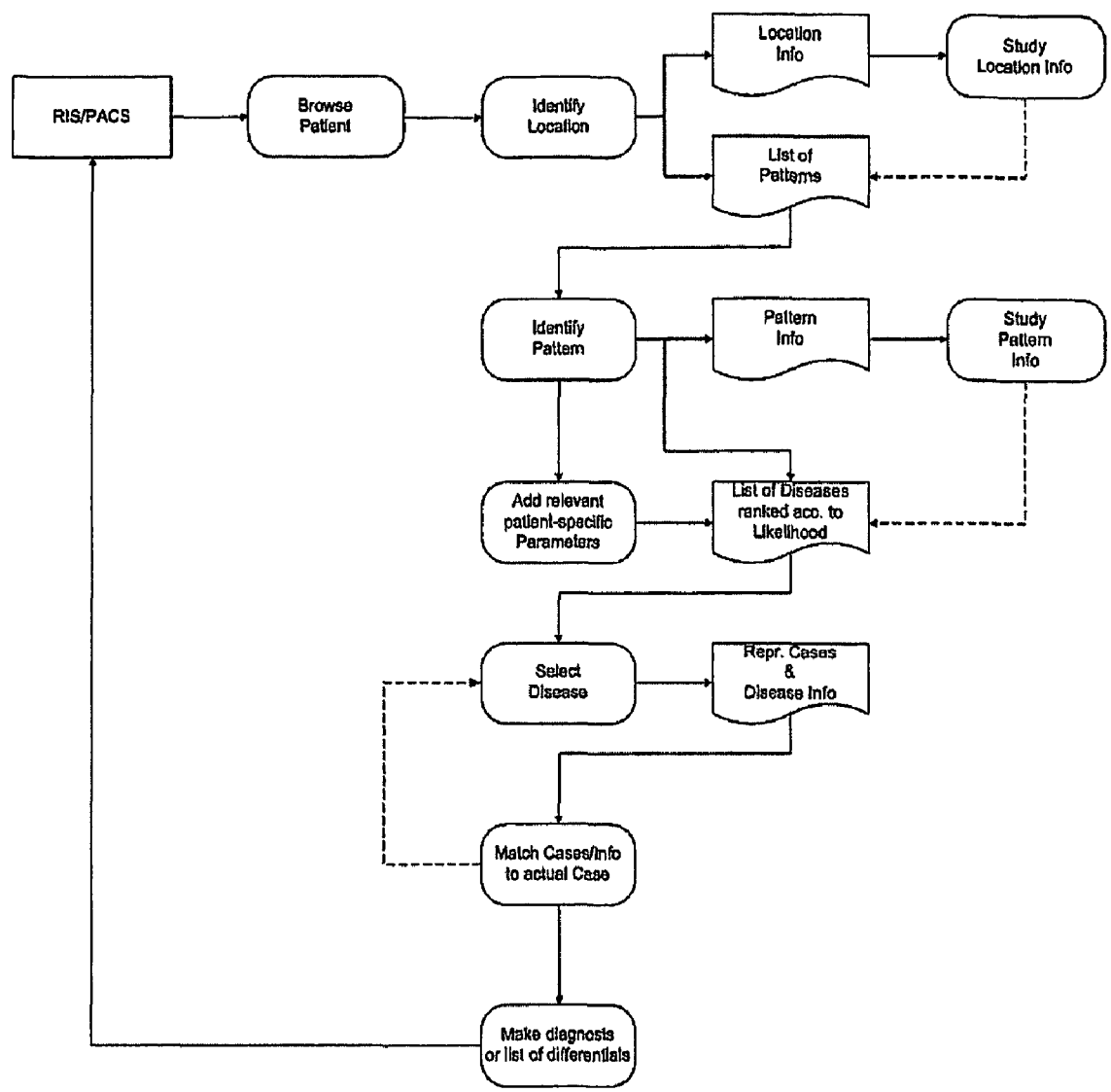
FIG. 16: Process Flow for Radiological care, using the invention.

One of the most distinctive and original parts of the solution is that it closely follows the natural work flow of a radiologist. This is depicted in FIG. 16.

Starting from the RIS, possibly linked to a PACS application, or another type of Medical Information System, the Radiologist chooses a patient and a corresponding image.

First, he identifies the organ group, location, and sublocation

Then, if needed, he studies location info (e.g., for anatomy help)

Then he identifies the pattern, by visual evaluation of the image

Then he may study pattern info (e.g. diagnostic value of a specific pattern)

Then he studies the list of possible diseases (ranked in decreasing order of likelihood) and selects a disease. For some specific combinations of sublocation and pattern, an intermediate step (providing patient-related information to the system) will be required.

Then he studies disease-specific information, and matches this information to his "actual" real-life case. Optionally, case examples may be studied too.

The latter process may be repeated for other diseases provided in the list

Finally, the user makes a diagnosis or list of differential diagnoses for the actual case and returns to the end user's application work list.

The present invention naturally follows the work flow of the radiologist by:

requesting the organ group, location, and sublocation requesting data regarding the pattern, matching this information to cases in the expert database.

repeating the process for several diseases provided in the list making a diagnosis or list of differential diagnoses for the actual case and returning to the end user's application work list.

Such similarity allowing a radiologist to seamlessly adopt the invention, with a minimum of adjustment to working practices.

Example 3

Technical Architecture

Basic Architecture

Figure 17:
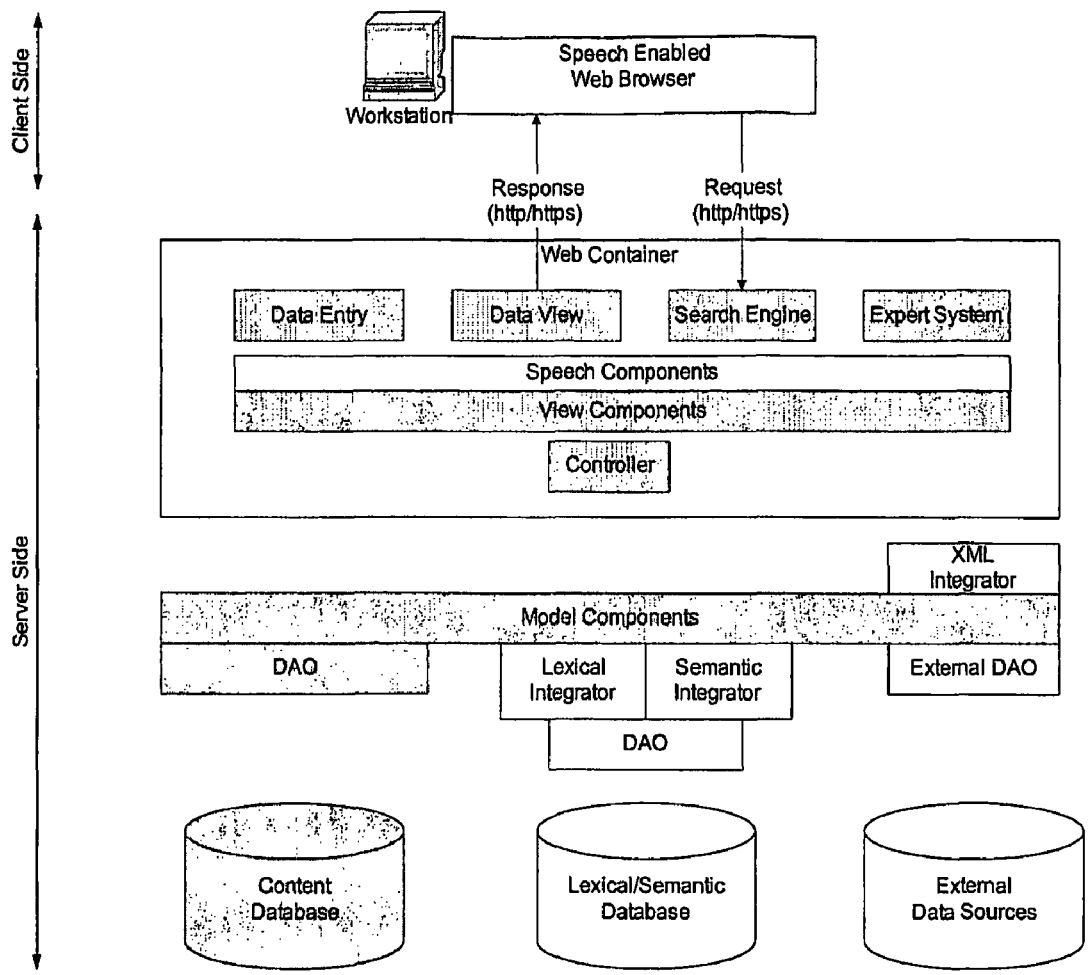
FIG. 17: Architecture for Online database Access. The grey components are those necessary for the basic set-up, the white components are extensions offering additional functionality.

An example of the technical architecture of the invention is shown in FIG. 17. Note that this architecture allows many technical implementations, some of which are specified in the description. However, other implementations are possible, and could be used, without modifying the basic notion of architecture itself.

The technical architecture for online database access is based on the MVC (Model-View-Controller) design pattern. In this pattern, the presentation layer is separated from the view layer, and as such, the presentation logic is split from the business logic. This allows the Model components to be easily reused when other View components are being used to display the model data.

An example of a basic implementation of the technical architecture is denoted by the grey components in FIG. 17. It consists of a content database (the Data Layer), a set of model components on top of a database access layer or DAO layer (the Model Layer), a set of controller components (the Controller Layer), a collection of view components, for several end user purposes such as data entry, data view, search engine or expert system (the View Layer), and finally a thin client in the form the browser. According to the invention, a technical implementation may comprise one or more of these components This architecture may most commonly be implemented using the J2EE or .Net platform. For our implementation, the J2EE platform has been chosen. Several frameworks are available, to enforce the use of the correct design patterns. Furthermore, several commercial providers such as IBM, Oracle or Sun offer Integrated Development Environments (IDE) that aid in the rapid development of applications in these platforms.

The Model layer may be implemented as a set of Java classes or Enterprise Java Beans. The controller may be based on the Struts Framework, currently the de facto standard for the development of scalable web applications, and the View layer may be implemented using jsp and html pages, also making use of the functionality provided by the Struts framework.

The web-container, necessary for running the Controller and View components, may be chosen from open source projects, or, for example, from the current high performance application servers from IBM, Oracle, Sun, etc. The choice depends on non-functional requirements such as high availability, performance, etc.

The implementation of the web-services for integration with 3rd party systems such as medical information systems, may make use of the J2EE platform. This allows integration with the majority of applications conforming to the web-services standards, including those implemented on a Microsoft platform. Integration with Microsoft .Net-based applications can be easily provided.

Extensions

Speech

In the view part of the architecture, there is an integration of web-based technology (dynamic html, using jsp), and speech technology. The speech technology is completely integrated within the graphical web components. The speech technology may makeuse of open standards, which allows the end user to plug-in their favourite implementation of these standards.

Lexical and Semantic Integrator

Integration with lexical and semantic databases is completely transparent to the end user. The integration may therefore be implemented on the model level, as part of the business logic of the system. Such means for implementing lexical and semantic functions are known to the skilled person.

External Data Sources

The system may be open to accepting 3rd party data. The most common way of integrating external data is by transforming it into XML, and by capturing the XML data, processing it and integrating it in the content database.

An XML integration component may, therefore, be included. As the delegation of the connection to either the internal or an external content database should preferably be completely transparent to the end user, this integration may be performed at the model level, becoming part of the business logic of the system.

Specific Entities

In the above, only general Entities have been defined. Below entities are defined that are involved in the natural workflow of the Radiologist. Extensions to other medical areas are possible, and can be easily plugged into the data model.

The database is centred around the notion of Locations, Patterns and Diseases. To this end, the model contains the central concept LocationPatternDiseases, which contains all combinations of the three main entities, around which three navigation axes have been defined. These axes allow navigation through the database starting from a particular point of view. The navigation axes are locations, with entry point Organ System patterns, with entry point Pattern Group diseases, with entry point Disease Group The most common navigation axis will be the location axis, as this will be the main entry point for most search and entry operations.

Figure 18:
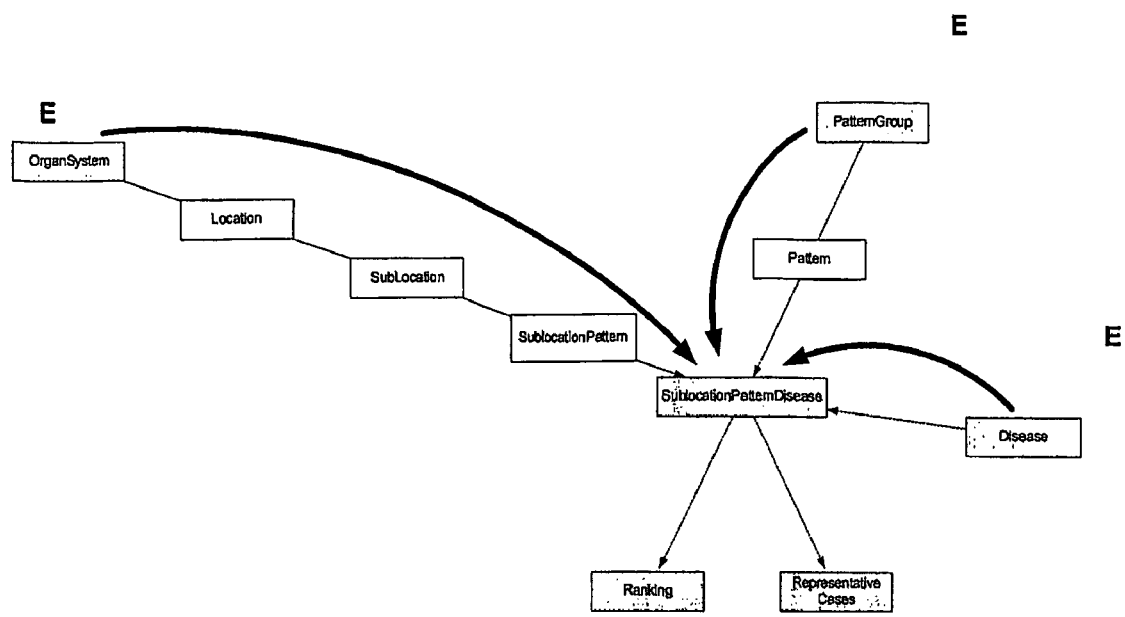
FIG. 18: Navigation axes (arrows) and Entry Points (E), towards central database Entity LocationPatternDiseases.
Figure 19:
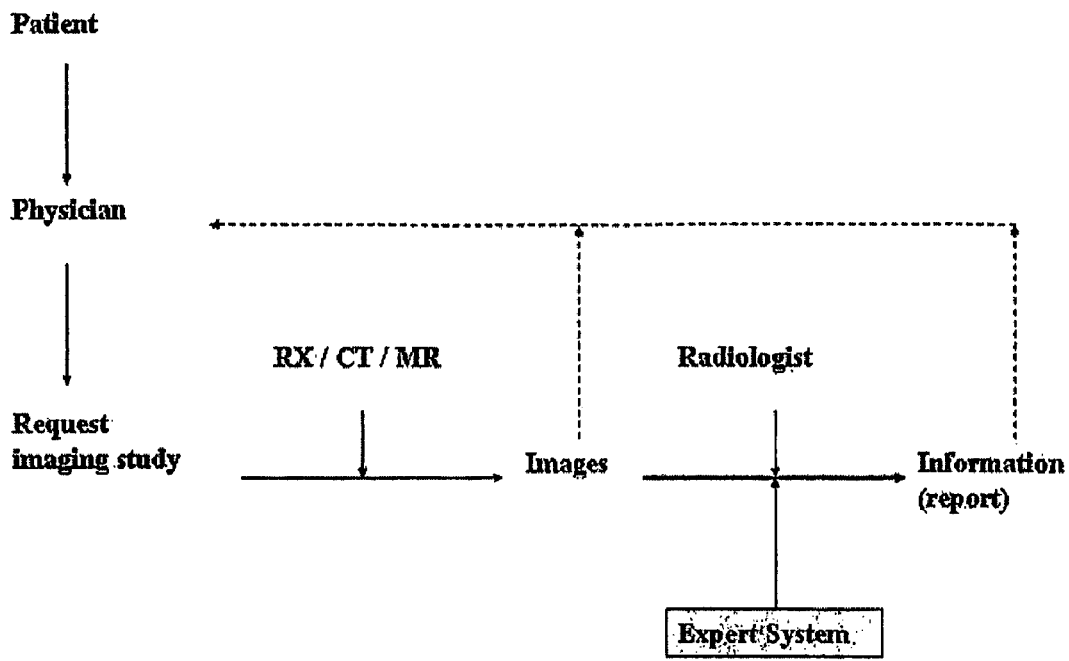
FIG. 19: The primary use of the database/expert system is to improve radiology work flow. As such, the invention improves the conversion of images to relevant information.

Both the central concept, and the navigation axes are shown in FIG. 18.

Example 5

Modifications

A system implementing a method of the invention as described herein may have one or more of the following modifications:

A modification in which the user navigates through the application using speech, i.e. the user can give specific commands with speech.

A modification in which the system is linked to the report dictation software used by the professional radiologist or other clinician. Preferably, an intelligent interface between the dictated text (interpreted by speech recognition technology) and the system, automatically extracts the most appropriate location and pattern out of the dictated text (using advanced pattern matching techniques, e.g. based on Bayesian Inference and Claude Shannon's principles of information theory) and navigates to the appropriate location/pattern. In this application, the radiologist does not have to interrupt his normal work flow at all. Instead, while dictating his/her report, the intelligent interface identifies the combination location/pattern best corresponding to the dictated words, and automatically displays the list of likely corresponding diseases. With one simple action, the user obtains access to further information about this disease.

A modification in which the system provides part of the information to the user via speech synthesis (e.g., asks questions, speaks about diseases, . . . )

A modification in which the system allows connection to other public or privately-owned databases. Such connection allows the user to obtain further information about a certain topic if desired. Therefore, the expert system enables direct access to the world wide web or to specific databases available online (certified by the producer, e.g. major radiological journals, Medline, . . . ) and allows specific simple or complex searches.

All translations of the above mentioned data/base expert system and its products in any other language.

Figure 21:
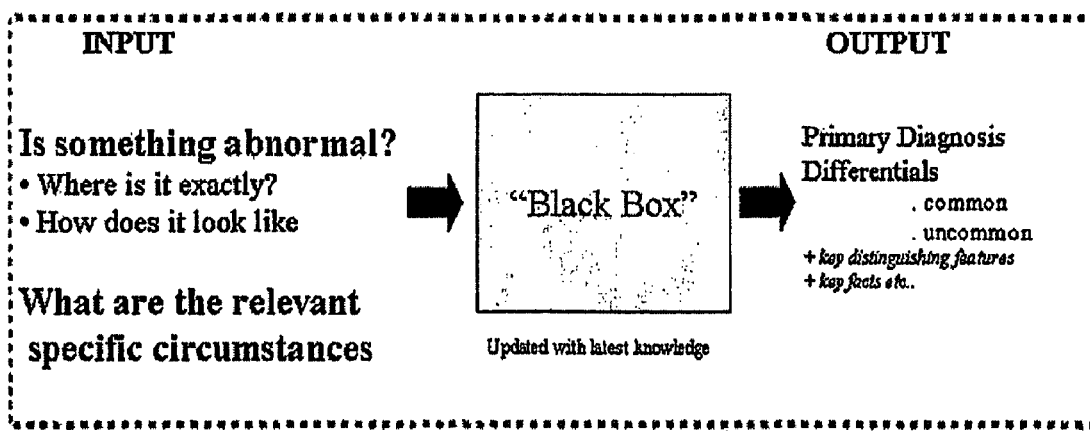
FIG. 21: Application of the methodology to other areas.

A similar system or method intended for use in other areas where key items from images and presentation of these key items are extracted, and placed in a structured way in a continuously updated data base/expert system. The method or system may have one or more features of the method and systems described herein. Inputted data may include location and pattern of an abnormality such as a defect in an object. An object can be any such as an engineered object, a body part, a building construction, a landscape feature etc. It can be any object susceptible of abnormality for which an abnormality pattern and its location can be characterised, preferably according to discrete categories. A multidimensional database would store lists of diagnoses linked to pattern and location. Other features such as the use of non-imaging data, importance ranking, lexicon, speech recognition, system integration, a multidimensional database product as described here are easily transferred a system and method applied to other areas such as objects. Such similar system leads to relevant information as output (FIG. 21). Examples of possible applications may be found in medicine, engineering, and many other areas.

Figure 22:
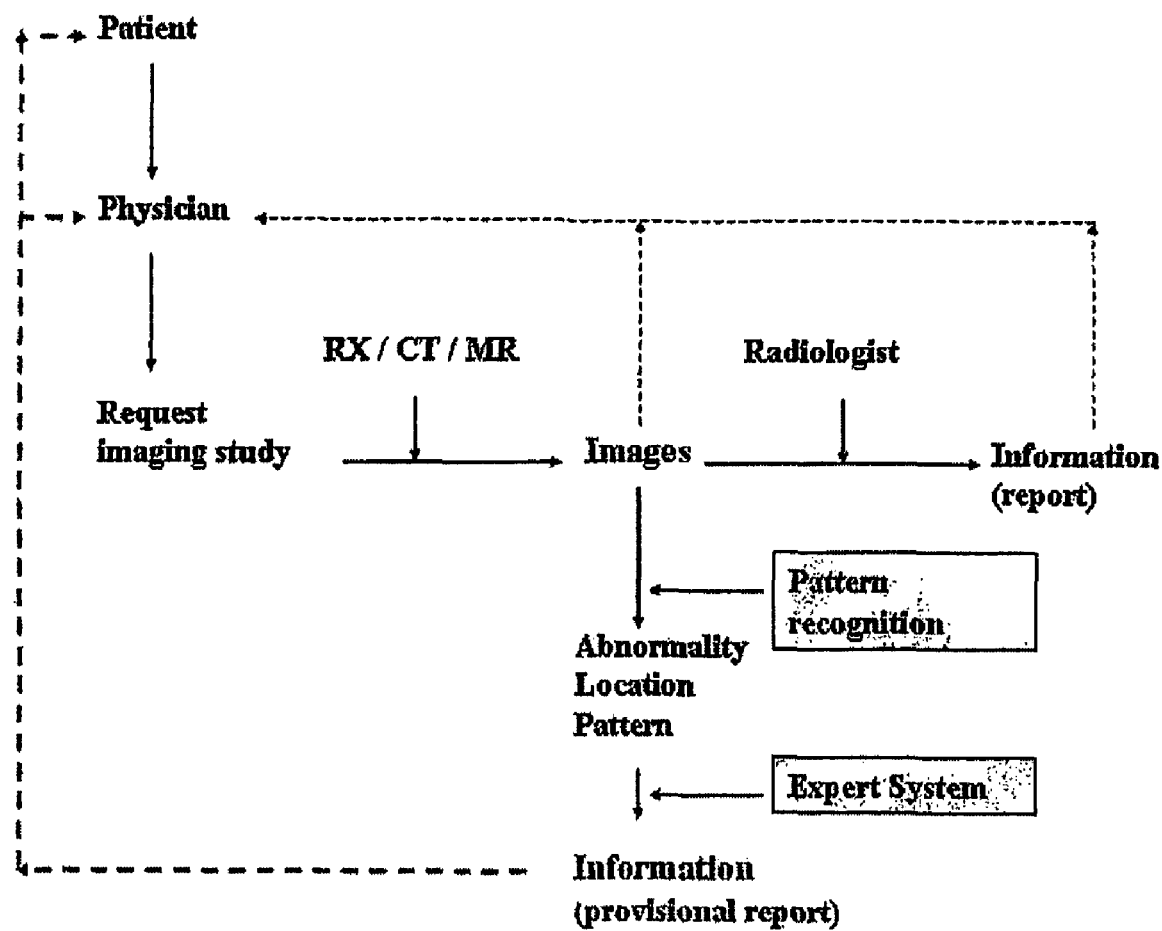
FIG. 22: Extension in which a pattern recognition module is added as a preliminary step. As such, the identification of the abnormality and its location and pattern occurs without human interaction. The resulting information can be sent automatically to the referring physician as a preliminary report.

A modification in which the system has an intelligent interface used for image recognition (pattern analysis). In this application, there is automatic definition of the location and pattern, and identification of the abnormality, so not needing the input of the radiologist (or other user). Also other combinations are possible, e.g. the radiologist identifies the abnormality and the system defines the location and pattern. Theoretically, this can be performed by pattern recognition or by computing the similarity between a new image and reference images in the database (each linked to a specific location/pattern/disease combination). This extension can be considered as a serial use of two "black boxes", one for identification of the abnormality and pattern analysis, and another one for conversion from image and patient-specific parameters to clinically relevant information (FIG. 22). In this model, the Invention is not used primarily as a facilitator of the radiologist's work, but as a parallel or even alternative circuit. Several applications may be possible. For example, the Invention may be used to provide a rapid provisional diagnosis. While typical process times in radiology (time between the actual examination and the arrival of the report where it is needed, i.e. in the hands of the referring physician) are measured in hours, the process time can be reduced to a few minutes or even seconds if the entire process occurs without human interaction. A rapid preliminary report can be sent to the referring physician (e.g. as an SMS to his/here mobile phone or message to another mobile device) allowing immediate action if needed. With this extension, the invention could be used not only to facilitate radiology work flow but to improve medical care directly. Potential "clients" would then not only be radiologists but all physicians.

Figure 23:
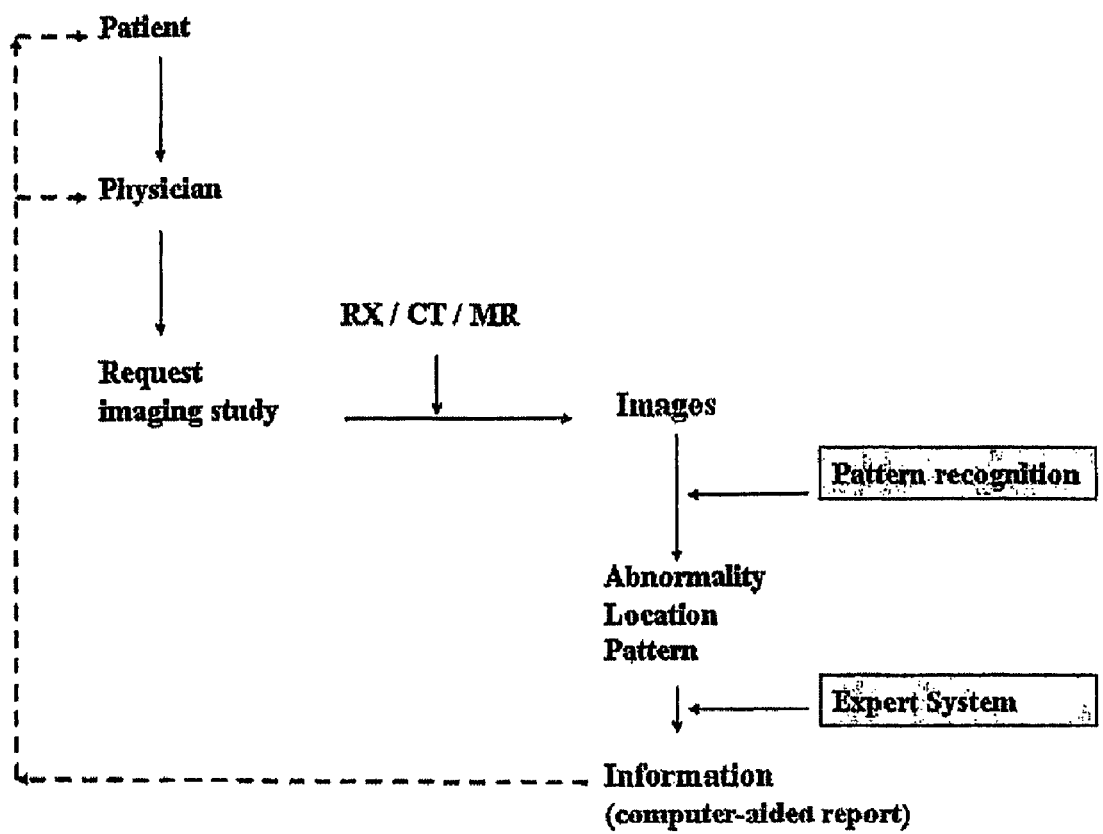
FIG. 23: Modification in which the extraction of relevant information out of medical images occurs without human interaction. A potential application could be large-scale screening studies in countries facing a shortage of radiologists.

Theoretically, it could also be possible that, for some applications, the computer-generated report is sent to the referring physician, or even directly to the patient, without need for supervision by a radiologist (FIG. 23). It can, for instance, be envisaged that certain screening studies conducted on large scale would be performed without human interaction, at least in a first step. Such a set-up could be a necessity, particularly in countries facing a shortage of radiologists. As an example, a virtual colonoscopy study could be interpreted by a computer and the result could be sent to the patient's mobile phone (or another device) immediately after the exam, with the additional comment that the patient has to consult his or her physician if the report is not completely normal.

SUMMARY OF SOME EMBODIMENTS THE INVENTION

One embodiment of the present invention is a method for assisting a physician with making a diagnosis based upon a medical image, the method comprising:
  providing a location template allowing for a selection of one of a plurality of body locations;
  receiving at least one selected body location;
  accessing via a digital computer a table of patterns observed at that body location, the table derived from a digital storage medium storing multi-dimensional data including body locations, patterns, and potential diagnoses;
  providing a pattern template allowing for selection of one or more patterns from the table of patterns;
  receiving one or more selected patterns;
  using the selected one or more patterns to access the storage medium so as to determine a list of possible diagnoses; and
  outputting the list of potential diagnoses.

Another embodiment of the present invention is a method as described above, further comprising receiving patient information.

Another embodiment of the present invention is a method as described above, wherein the potential diagnoses are ordered according to likelihood.

Another embodiment of the present invention is a method as described above, wherein the potential diagnoses are ordered taking into account patient information.

Another embodiment of the present invention is a method as described above, wherein the pattern template provides displayable images of patterns in the table.

Another embodiment of the present invention is a method as described above, wherein the patterns are placed in relevant order on the pattern template based upon the selected body location.

Another embodiment of the present invention is a method as described above, wherein using the selected one or more patterns to access the storage medium includes locating within a multi-dimensional database the one or more potential diagnoses based upon the one or more selected patterns and locations.

Another embodiment of the present invention is a method as described above, wherein locating is achieved by extracting data from the multi-dimensional database at an intersection of pattern and body location planes crossed by the selected body location and pattern.

Another embodiment of the present invention is a system for assisting a physician with making a diagnosis based upon a medical image, the system comprising:
  a processor that outputs one or more templates for display on a display device and receives user selections in response to presentation of the templates on the display device;
  a digital storage medium containing multi-dimensional data including body locations of a medical image, patterns, and one or more potential diagnoses;

wherein the processor outputs one or more diagnoses retrieved from the digital storage medium based upon the user selections.

Another embodiment of the present invention is a system for assisting a physician with making a diagnosis as described above, wherein the multi-dimensional data is stored in a multi-dimensional database.

Another embodiment of the present invention is a system for assisting a physician with making a diagnosis as described above, wherein the one or more templates are stored in memory and are retrieved from memory by the processor.

Another embodiment of the present invention is a system for assisting a physician with making a diagnosis as described above, wherein the processor outputs a body location template that allows for user selection of a location on a human body associated with a medical image.

Another embodiment of the present invention is a system for assisting a physician with making a diagnosis as described above, wherein the processor outputs a pattern template based upon a user selection of a body location and the pattern template allows for user selection of one or more patterns by the user.

Another embodiment of the present invention is a system for assisting a physician with making a diagnosis as described above, wherein the digital storage medium contains a multi-dimensional database and the processor locates the one or more potential diagnoses in the multi-dimensional database based upon user selection of one or more body locations and one or more patterns.

Another embodiment of the present invention is a system for assisting a physician with making a diagnosis as described above, wherein the digital storage medium and the processor may be in communication over a network.

Another embodiment of the present invention is a system for assisting a physician with making a diagnosis as described above, further comprising:
- a display device coupled to a computer system for receiving and displaying the output from the processor.

Another embodiment of the present invention is a system for assisting a physician with making a diagnosis as described above, wherein the computer system and display device are in communication with the processor over a network.

Another embodiment of the present invention is a system for determining a diagnosis based upon a medical image, the system comprising:
- a processor for receiving a signal related to the medical image containing information regarding location of the medical image within the human body and regarding a pattern within the image; and
- a database containing a plurality of potential diagnoses wherein each diagnosis is associated with at least one location and one pattern;

wherein the processor retrieves one or more diagnoses from the database based upon the location and the pattern received in the signal and provides the one or more diagnoses as an output.

Another embodiment of the present invention is a system for determining a diagnosis based upon a medical image as described above wherein the diagnostic database is a multi-dimensional database.

Another embodiment of the present invention is a system for determining a diagnosis based upon a medical image as described above wherein the processor outputs a location template that allows for user selection of a location on a human body associated with a medical image.

Another embodiment of the present invention is a system for determining a diagnosis based upon a medical image as described above wherein the processor outputs a pattern template based upon a user selection of a location and the pattern template allows for user selection of one or more patterns by the user that represent patterns found in the medical image.

Another embodiment of the present invention is a further method for assisting a physician with making a diagnosis based upon a medical image, the method comprising:
- providing a template for making a selection of one of a plurality of locations of a human body and for making a selection of one or more of a plurality of patterns;
- receiving a signal representative of a selected body location and a selected pattern; and
- outputting an output signal containing one or more potential diagnoses retrieved from a database that relates body locations, patterns and potential diagnoses.

Another embodiment of the present invention is a further method as described above, further comprising receiving a signal representative of patient information.

Another embodiment of the present invention is a further method as described above, wherein the potential diagnoses are ordered according to likelihood.

Another embodiment of the present invention is a further method as described above, wherein the potential diagnoses are ordered taking into account patient information.

Another embodiment of the present invention is a further method as described above, wherein the template provides textual information displayable on a display device regarding patterns typically representative of medical images that are associated with the selected body location.

Another embodiment of the present invention is a further method as described above, wherein the output signal is displayable on a display device.

Another embodiment of the present invention is a further method as described above, wherein the method is performed on a computer system.

Another embodiment of the present invention is a further method as described above, wherein the patterns are ordered on the template based upon the selected location.

Another embodiment of the present invention is a further method as described above, further comprising:
- locating within a multi-dimensional database at least the one or more potential diagnoses based upon the selected pattern and selected body location.

Another embodiment of the present invention is a computer program product having computer readable code thereon for use with a computer, the computer program product assisting a physician with making a diagnosis based upon a medical image, the computer code comprising:
- computer code for providing a location template allowing for a selection of one or more locations of a human body;
- computer code for receiving a signal representative of at least one selected body location;
- computer code for providing a pattern template allowing for selection of one or more patterns, wherein the pattern template that is provided is based upon the selection of the body location;
- computer code for receiving a signal representative of a selected pattern;
- computer code for transmitting a signal containing one or more diagnoses based upon the one or more selected body locations and patterns.

Another embodiment of the present invention is the computer program product as described above, further comprising:
- computer code for receiving a signal representative of patient information.

Another embodiment of the present invention is a computer program product as described above, wherein the diagnoses are ordered according to likelihood.

Another embodiment of the present invention is a computer program product as described above, wherein the diagnoses are ordered taking into account patient information.

Another embodiment of the present invention is a computer program product as described above, wherein the pattern template provides images of patterns that are associated with the selected location.

Another embodiment of the present invention is a computer program product as described above, wherein the transmitted signal is displayable on a display device.

Another embodiment of the present invention is a computer program product as described above, further comprising:
computer code for ordering the morphological patterns on the pattern template based upon the selected body location.

Another embodiment of the present invention is a computer program product as described above, further comprising:
computer code for locating within a multi-dimensional database at least the one or more diagnoses based upon the one or more selected patterns and body locations.

Another embodiment of the present invention is an alternative computer program product having computer readable code thereon for use with a computer, the computer program product assisting a physician with making a diagnosis based upon a medical image, the method comprising:
computer code for providing a template allowing for a selection of one of a plurality of locations of a human body and allowing for a selection of one or more of a plurality of patterns;
computer code for receiving a signal representative of a selected body location and a selected pattern; and
computer code for outputting an output signal containing one or more potential diagnoses retrieved from a multi-dimensional database that associates body locations, patterns and diagnoses.

Another embodiment of the present invention is an alternative computer program product according as described above, further comprising:
computer code for receiving a signal representative of patient information.

Another embodiment of the present invention is an alternative computer program product according as described above, further comprising computer code for ordering the diagnoses according to likelihood.

Another embodiment of the present invention is an alternative computer program product according as described above, further comprising computer code for ordering the diagnoses taking into account patient information.

Another embodiment of the present invention is an alternative computer program product according as described above, wherein the template provides images of patterns that are associated with the selected location.

Another embodiment of the present invention is an alternative computer program product according as described above, wherein the output signal is displayable on a display device.

Another embodiment of the present invention is an alternative computer program product according as described above, further comprising computer code for ordering the patterns on the template based upon the selected body location.

Another embodiment of the present invention is an alternative computer program product according as described above, further comprising:
computer code for locating within a multi-dimensional database at least the one or more diagnoses based upon the one or more selected patterns and body locations.

One embodiment of the present invention is a method for evaluating at least one abnormality in one or more medical images of a subject comprising:
(a) determining the location of each abnormality from pre-defined selection,
(b) determining the pattern of each abnormality from pre-defined selection,
(c) accessing a multidimensional database comprising data of patterns, locations, and conditions associated therewith, in which
data of each of patterns, locations, and conditions is comprised in separate dimension(s), and
characteristic information for patterns, locations, and conditions is organised into discrete categories,
(d) extracting from the multidimensional database list of conditions corresponding to the imaging data determined in steps (a) and (b), and
(e) providing an evaluation of abnormality using list obtained in step (d).

Another embodiment of the present invention is a method as described above wherein the multidimensional database further comprises data regarding the discriminative value of one or more combinations of location and pattern.

Another embodiment of the present invention is a method as described above wherein the list of conditions is ranked according to probability.

Another embodiment of the present invention is a method as described above wherein a low discriminative value of a selected pattern generates a request to use an alternative approach.

Another embodiment of the present invention is a method as described above wherein the multidimensional database comprises one or more additional dimensions corresponding to non-imaging medical data of the subject.

Another embodiment of the present invention is a method as described above wherein said non-imaging medical data comprises one or more of patient sex, age, ethnicity, immune status, and oncological antecedents.

Another embodiment of the present invention is a method as described above wherein a request is generated to provide non-imaging medical data, when the database indicates such data can adjust the reported probability of a condition.

Another embodiment of the present invention is a method as described above wherein the reported probability of a condition is adjusted according to non-imaging data provided.

Another embodiment of the present invention is a method as described above, wherein providing at least part of the non-imaging and/or imaging data comprises the use of speech recognition.

Another embodiment of the present invention is a method as described above, wherein at least part of non-imaging and/or imaging data is provided by means of an interaction with the method.

Another embodiment of the present invention is a method as described above, wherein at least part of the data is provided by means of a speech enabled interaction with the method.

Another embodiment of the present invention is a method as described above, wherein the pre-defined selections are comprised in a set of terms represented by a lexicon, wherein the lexicon can be changed according to the understanding or language of the operator.

Another embodiment of the present invention is a method as described above wherein the imaging data and non-imaging are provided to the method via another application.

Another embodiment of the present invention is a method as described above wherein the list of diagnoses is provided by the method to another application.

Another embodiment of the present invention is a method as described above wherein said other application is a Radiology Information Systems and/or Picture Archive and Communication Systems.

Another embodiment of the present invention is a method as described above, wherein the method accesses at least one other database.

Another embodiment of the present invention is a system for evaluating at least one abnormality in one or more medical images of a subject comprising:
  (a) means for inputting a location determined for each abnormality from a pre-defined selection,
  (b) means for inputting a pattern determined for each abnormality from pre-defined selection,
  (c) means for accessing a multidimensional database comprising data of patterns, locations, and conditions associated therewith, in which
     data of each of patterns, locations, and conditions is comprised in separate dimension(s), and
     characteristic information for patterns, locations, and conditions is organised into discrete categories, and
  (d) means for extracting from the multidimensional database a list of conditions corresponding to the imaging data determined in steps (a) and (b).

Another embodiment of the present invention is a system as described above, further comprising the multidimensional database of step (c).

Another embodiment of the present invention is a system as described above wherein the multidimensional database further comprises data regarding the discriminative value of one or more combinations of location and pattern.

Another embodiment of the present invention is a system as described above comprising means to rank the list the condition according to probability.

Another embodiment of the present invention is a system as described above comprising means to generate a request to use an alternative approach when a low discriminative value pattern is inputted in step (b).

Another embodiment of the present invention is a system as described above wherein the multidimensional database comprises one or more additional dimensions corresponding to non-imaging medical data of the subject.

Another embodiment of the present invention is a system as described above wherein said non-imaging medical data comprises one or more of patient sex, age, ethnicity, immune status, and oncological antecedents.

Another embodiment of the present invention is a system as described above comprising means to generate a request to provide non-imaging medical data, when the database indicates such data can adjust the reported probability of a condition.

Another embodiment of the present invention is a system as described above comprising means to adjust the reported probability of a condition according to non-imaging data provided.

Another embodiment of the present invention is a system as described above, comprising speech recognition means.

Another embodiment of the present invention is a system as described above, comprising interactive means.

Another embodiment of the present invention is a system as described above, comprising dictated interactive means.

Another embodiment of the present invention is a system as described above, comprising means to change the lexicon used in the pre-defined selection in steps (a) and (b) according to the understanding or language of the operator.

Another embodiment of the present invention is a system as described above comprising means to receive the imaging data and/or non-imaging data from another application.

Another embodiment of the present invention is a system as described above comprising means to provide a list of diagnoses to another application.

Another embodiment of the present invention is a system as described above wherein said other application is a Radiology Information Systems and/or Picture Archive and Communication Systems.

Another embodiment of the present invention is a system as described above, comprising means to access at least one other database.

Another embodiment of the present invention is a system as described above comprising an architecture comprising one or more of:
  data layer,
  set of model components on top of a database access layer,
  set of controller components, and
  set of view components.

Another embodiment of the present invention is a system as described above comprising units of information linked to the items location, pattern, and disease, or to specific combinations of these items.

Another embodiment of the present invention is a system as described above in which information linked to the item location includes one or more of the following information units: anatomy key facts, non-anatomy key facts, anatomy, anatomic variants, non-anatomy facts.

Another embodiment of the present invention is a system as described above in which information linked to the item disease includes one or more of the following information units: description, synonyms, abbreviations incidence, age/sex distribution, etiology, associated disease, organ(s) typically affected, gross pathology, microscopic pathology, histologic subtypes, clinical presentation, treatment and prognosis, imaging findings: general remarks, preferred imaging test(s) to diagnose this disease, suggested non-imaging test(s) to diagnose this disease.

Another embodiment of the present invention is a system as described above in which information linked to a combination of a location and a pattern includes one or more of the following information units: technical remarks, prototype example, diagnostic value of this pattern, diagnostic checklist associated with this pattern, comment, variants of this pattern and their significance.

Another embodiment of the present invention is a system as described above in which information linked to a combination of a location, a pattern, and a disease includes one or more of the following information units: key discriminative imaging findings, key discriminative non-imaging findings.

Another embodiment of the present invention is a system as described above comprising means for an operator to remotely access the system.

Another embodiment of the present invention is a system as described above, comprising at least one web server.

Another embodiment of the present invention is a system as described above comprising means to generate non-interactive cc interactive publications of data in the database.

Another embodiment of the present invention is a system as described above comprising means to link the database to an application capable of analysing medical images, identifying an abnormality and/or identifying the pattern and location corresponding to an abnormality, either automatically or semi-automatically, and in which the resulting information provides part or all of the imaging data of steps (a) and (b).

Another embodiment of present invention is a system as described above comprising means to navigating along different navigation axes by choosing either location, pattern, or disease as entry point.

Another embodiment of the present invention is a system for navigating a multidimensional medical database comprising:
(a) means for accessing a multidimensional database comprising data of patterns, locations, and conditions associated therewith, in which
  data of each of patterns, locations, and conditions is comprised in separate dimension(s), and
  characteristic information on patterns, locations, and conditions is organised into discrete categories,
(d) means for inputting navigational information, and
(c) means for extracting from the multidimensional database a list of conditions patterns, locations depending on the navigational information.

Another embodiment of the present invention is a system as described above further comprising one or more features as described above.

Another embodiment of the present invention is a system as described above comprising means for providing results of navigation as one or more of text, numbers, case examples, drawings, computer generated graphics, video clips, or any other type of relevant output.

Another embodiment of the present invention is a multidimensional database comprising data of patterns, locations, and conditions associated therewith, in which
  data of each of patterns, locations, and conditions are comprised in separate dimension(s), and
  characteristic information on patterns, locations, and conditions is organised into discrete categories, Another embodiment of the present invention is a multidimensional database as described above wherein data has been validated by at least one medical expert.

Another embodiment of the present invention is a multidimensional database as described above further comprising one or more the features as described above.

Another embodiment of the present invention is a computer program on a computer readable medium capable of performing a method as described above.

Another embodiment of the present invention is a computer program on a computer readable medium capable of providing functionality of a system as described above.

Another embodiment of the present invention is a computer program on a computer readable medium capable of providing a multidimensional database as described above.

Another embodiment of the present invention is a method for evaluating at least one abnormality in one or more images of an object, comprising:
(a) determining the location of each abnormality from pre-defined selection,
(b) determining the pattern of each abnormality from pre-defined selection,
(c) accessing a multidimensional database comprising data of patterns, locations, and diagnoses associated therewith, in which
  data of each of patterns, locations, and diagnoses is comprised in separate dimension(s), and
  characteristic information for patterns, locations, and diagnoses is organised into discrete categories,
(d) extracting from the multidimensional database a list of diagnoses corresponding to the imaging data determined in steps (a) and (b), and
(e) providing an evaluation of abnormality using list obtained in step (d).

Another embodiment of the present invention is a method as described above wherein the multidimensional database further comprises data regarding the discriminative value of one or more combinations of location and pattern.

Another embodiment of the present invention is a method as described above wherein the list of diagnoses is ranked according to probability.

Another embodiment of the present invention is a method as described above wherein a low discriminative value of a selected pattern generates a request to use an alternative approach.

Another embodiment of the present invention is a method as described above wherein the multidimensional database comprises one or more additional dimensions corresponding to relevant non-imaging data.

Another embodiment of the present invention is a method as described above wherein a request is generated to provide non-imaging data, when the database indicates such data can adjust the reported probability of a condition.

Another embodiment of the present invention is a method as described above wherein the reported probability of a diagnosis is adjusted according to non-imaging data provided.

Another embodiment of the present invention is a method as described above, wherein the pre-defined selections are comprised in a set of terms represented by a lexicon, wherein the lexicon can be changed according to the understanding or language of the operator.

Another embodiment of the present invention is a system for evaluating at least one abnormality in one or more images of an object comprising:
(a) means for inputting a location determined for each abnormality from a pre-defined selection,
(b) means for inputting a pattern determined for each abnormality from pre-defined selection,
(c) means for accessing a multidimensional database comprising data of patterns, locations, and diagnoses associated therewith, in which
  data of each of patterns, locations, and diagnoses is comprised in separate dimension(s), and
  characteristic information for patterns, locations, and diagnoses is organised into discrete categories, and
(d) means for extracting from the multidimensional database a list of diagnoses corresponding to the imaging data determined in steps (a) and (b).

Another embodiment of the present invention is a system as described above, further comprising the multidimensional database of step (c).

Another embodiment of the present invention is a system as described above wherein the multidimensional database further comprises data regarding the discriminative value of one or more combinations of location and pattern.

Another embodiment of the present invention is a system as described above comprising means to rank the list the condition according to probability.

Another embodiment of the present invention is a system as described above comprising means to generate a request to use an alternative approach when a low discriminative value pattern is inputted in step (b).

Another embodiment of the present invention is a system as described above wherein the multidimensional database comprises one or more additional dimensions corresponding to non-imaging data of the object.

Another embodiment of the present invention is a system as described above comprising means to generate a request to provide non-imaging data, when the database indicates such data can adjust the reported probability of a condition.

Another embodiment of the present invention is a system as described above comprising means to adjust the reported probability of a condition according to non-imaging data provided.

Another embodiment of the present invention is a system as described above, comprising means to change the lexicon used in the pre-defined selection in steps (a) and (b) according to the understanding or language of the operator.

Another embodiment of the present invention is a computer program held on a computer readable medium capable of performing a method as described above.

Another embodiment of the present invention is a computer program on a computer readable medium capable of providing functionality of a system as described above.

Another embodiment of the present invention is a method for entering data in a multidimensional database as described above by providing an indication of a location and pattern of an abnormality observed in a medical image of a diagnosed subject, and a disease associated therewith.

Another embodiment of the present invention is a method for entering data as described above wherein an indication of the pattern category is provided for said pattern, which is the morphology of the abnormality, uptake of contrast media by the abnormality or functional profile of the abnormality.

Another embodiment of the present invention is a method for entering data as described above wherein an indication of the group is provided for a pattern of said morphological pattern category, which group is selected from focal abnormalities, diffuse disease or abnormal size and anatomy.

Another embodiment of the present invention is a method for entering data as described above wherein an indication of the group is provided for a pattern of said uptake of contrast media pattern category, which group is selected from focal abnormalities or diffuse disease.

Another embodiment of the present invention is a method for entering data as described above wherein an indication of the group is provided for a pattern of functional profile pattern category which group is selected from blood flow or muscular contraction.

Another embodiment of the present invention is a method for entering data as described above wherein an indication of the modality of the medical image is provided with the pattern.

Another embodiment of the present invention is a method for entering data as described above wherein an indication of the organ system, location within said organ and optionally sublocation is provided.

Another embodiment of the present invention is a method for entering data as described above wherein the organ system and location is selected from a list such as in Table 1.

Another embodiment of the present invention is a method for entering data as described above wherein non-imaging data is additionally provided, corresponding to one or more of age, sex, area, immune status, oncologic antecedents.

Another embodiment of the present invention is a method for entering data as described above wherein possible choices of age, sex, area, immune status, oncologic antecedents are selected from the list in Table 3.

Another embodiment of the present invention is a method for entering data as described above wherein the number of diseases is between 1 and 5.

Another embodiment of the present invention is a method for entering data as described above wherein the list of possible diseases is reduced by combining two or more patterns.

Another embodiment of the present invention is a method for entering data as described above wherein the list of possible diseases is reduced by adding one or more details to a pattern.

Another embodiment of the present invention is a method for entering data as described above wherein the list of possible diseases is increased by integrating a pattern into a more general pattern.

Another embodiment of the present invention is a method for entering data as described above performed by an expert.

Another embodiment of the present invention is a method for entering data as described above comprising the steps of providing an indication of:
(a) name and organ system assigned to the expert,
(b) pattern,
(c) location of said pattern and optionally the sublocation,
(d) diagnostic value of said pattern,
(e) image typical of the pattern,
(f) names of diseases most commonly corresponding to the pattern, in order of likelihood,
(g) likelihood of a disease when the pattern of step (b) is observed,
(h) likelihood that a disease presents with that pattern,
(i) discriminative findings.

The invention claimed is:

1. Method for evaluating at least one abnormality in one or more medical images of a subject comprising:
   (a) determining the location of each abnormality and selecting it from a pre-defined selection of abnormality locations, which determining and selecting are performed by an operator,
   (b) determining the pattern of each abnormality and selecting it from a pre-defined selection of abnormality patterns, which determining and selecting are performed by an operator,
   (c) accessing a multidimensional database comprising at least three dimensions, said multidimensional database comprising data of patterns, locations, and conditions associated therewith, in which
      data of each of patterns, locations, and conditions are comprised in separate dimensions, and
      characteristic information for patterns, locations, and conditions is organized into discrete categories,
   (d) extracting from the multidimensional database, using a processor, a list of conditions corresponding to the operator selections determined in steps (a) and (b), and
   (e) providing an evaluation of abnormality using the list obtained in step (d).

2. Method according to claim 1 wherein the list of conditions is ranked according to probability.

3. Method according to claim 1, wherein the pre-defined selections are comprised in a set of terms represented by a lexicon, wherein the lexicon can be changed according to the understanding or language of the operator.

4. Computer program on a non-transitory computer readable medium capable of performing a method of claim 1.

5. Method according to claim 1, wherein the pre-defined selection for the location of each abnormality and for the pattern of each abnormality is a textual selection.

6. Method according to claim 1 wherein the multidimensional database further comprises data regarding the discriminative value of one or more combinations of location and pattern.

7. Method according to claim 6 wherein a low discriminative value of a selected pattern generates a request to use an alternative approach.

8. Method according to claim 1 wherein the multidimensional database comprises one or more additional dimensions corresponding to non-imaging medical data of the subject.

9. Method according to claim 8 wherein said non-imaging medical data comprises one or more of patient sex, age, ethnicity, immune status, and oncological antecedents.

10. Method according to claim 8 wherein a request is generated to provide non-imaging medical data, when the database indicates such data can adjust the reported probability of a condition.

11. Method according to claim 8 wherein the reported probability of a condition is adjusted according to non-imaging data provided.

12. System for evaluating at least one abnormality in one or more medical images of a subject comprising:
    (a) means for inputting by an operator a location determined for each abnormality from a pre-defined selection,
    (b) means for inputting by an operator a pattern determined for each abnormality from a pre-defined selection,
    (c) means for accessing a multidimensional database comprising at least three dimensions, said multidimensional database comprising data of patterns, locations, and conditions associated therewith, in which
        data of each of patterns, locations, and conditions are comprised in separate dimensions, and
        characteristic information for patterns, locations, and conditions is organized into discrete categories, and
    (d) means for extracting from the multidimensional database a list of conditions corresponding to the imaging data determined in steps (a) and (b).

13. System according to claim 12, further comprising the multidimensional database of step (c).

14. System according to claim 12 comprising means to rank the list of conditions according to probability.

15. System according to claim 12, comprising means to change the lexicon used in the pre-defined selection in steps (a) and (b) according to the understanding or language of the operator.

16. System according to claim 12, comprising means to access at least one other database.

17. System according to claim 12 comprising an architecture comprising one or more of:
    data layer,
    set of model components on top of a database access layer,
    set of controller components, and
    set of view components.

18. System according to claim 12 comprising means to link the database to an application capable of analysing medical images, identifying an abnormality and/or identifying the pattern and location corresponding to an abnormality, either automatically or semi-automatically, and in which the resulting information provides part or all of the imaging data of steps (a) and (b).

19. Computer program on a non-transitory computer readable medium capable of providing functionality of a system according to claim 12.

20. System according to claim 12 comprising units of information linked to the items location, pattern, and disease, or to specific combinations of these items.

21. System according to claim 20 in which information linked to the item location includes one or more of the following information units: anatomy key facts, non-anatomy key facts, anatomy, anatomic variants, non-anatomy facts.

22. System according to claim 20 in which information linked to the item disease includes one or more of the following information units: description, synonyms, abbreviations, incidence, age/sex distribution, etiology, associated disease, organ(s) typically affected, gross pathology, microscopic pathology, histologic subtypes, clinical presentation, treatment and prognosis, imaging findings: general remarks, preferred imaging test(s) to diagnose this disease, suggested non-imaging test(s) to diagnose this disease.

23. System according to claim 20 in which information linked to a combination of a location and a pattern includes one or more of the following information units: technical remarks, prototype example, diagnostic value of this pattern, diagnostic checklist associated with this pattern, comment, variants of this pattern and their significance.

24. System according to claim 20 in which information linked to a combination of a location, a pattern, and a disease includes one or more of the following information units: key discriminative imaging findings, key discriminative non-imaging findings.

25. System according to claim 12 wherein the multidimensional database further comprises data regarding the discriminative value of one or more combinations of location and pattern.

26. System according to claim 25 comprising means to generate a request to use an alternative approach when a low discriminative value pattern is inputted in step (b).

27. System according to claim 25 wherein the multidimensional database comprises one or more additional dimensions corresponding to non-imaging medical data of the subject.

28. System according to claim 27 wherein said non-imaging medical data comprises one or more of patient sex, age, ethnicity, immune status, and oncological antecedents.

29. System according to claim 27 comprising means to generate a request to provide non-imaging medical data, when the database indicates such data can adjust the reported probability of a condition.

30. System according to claim 27 comprising means to adjust the reported probability of a condition according to non-imaging data provided.

* * * * *